United States Patent
Nielsen et al.

(10) Patent No.: US 6,300,318 B1
(45) Date of Patent: Oct. 9, 2001

(54) ANTIBACTERIAL AND ANTIBIOTIC METHODS USING PEPTIDE NUCLEIC ACIDS AND PHARMACEUTICAL COMPOSITIONS THEREFOR

(75) Inventors: Peter E. Nielsen, Hjortevanget 509, DK 2980, Kokkedal; Liam Good, Copenhagen, both of (DK)

(73) Assignee: Peter E. Nielsen (DK)

( * ) Notice: Subject to any disclaimer, the term of this patent is extended or adjusted under 35 U.S.C. 154(b) by 0 days.

(21) Appl. No.: 08/932,140

(22) Filed: Sep. 16, 1997

(51) Int. Cl.[7] .......................... A01N 43/00; A01N 37/18; G01N 33/566; C12Q 1/68

(52) U.S. Cl. ................... 514/44; 435/6; 436/501; 514/2

(58) Field of Search ................. 435/6; 436/501; 514/2, 44; 935/77, 78

(56) References Cited

U.S. PATENT DOCUMENTS

| | | | |
|---|---|---|---|
| 5,220,014 | 6/1993 | Ackerman et al. | 536/24.5 |
| 5,447,914 | 9/1995 | Travis et al. | 514/16 |
| 5,539,082 | 7/1996 | Nielsen et al. | 530/300 |
| 5,539,083 | 7/1996 | Cook et al. | 530/333 |
| 5,641,625 | 6/1997 | Ecker et al. | 435/6 |
| 5,645,985 | 7/1997 | Froehler et al. | 435/6 |
| 5,650,321 | 7/1997 | Levy | 435/252.3 |

FOREIGN PATENT DOCUMENTS

| | | |
|---|---|---|
| WO 86/05518 | 9/1986 | (WO) . |
| WO 92/20702 | 11/1992 | (WO) . |

OTHER PUBLICATIONS

Beran, M. et al., "Substituted ω–(4–Oxo–3, 4–Dihydro–5–Pyrimidinyl) Alkanoic Acids, Their Derivatives and Analogues", *Collect. Czech. Chem. Commun.*, 1983, 48, 292–298.

Brigotti, M., et al., "Oligonucleotides Complementary to the α–Sarcin Domain of 28S rRNA Inhibit Cell–free Protein Synthesis", *Biochem. Mol. Biol. Int.*, 1993, 31, 897–903.

Chen, H.Z. et al., "Prokaryotic Coupled Transcription–Translation", *Methods in Enzymol.*, 1983, 101, 674–690.

Christensen, L., et al., "Solid–phase Synthesis of Peptide Nucleic Acids", *J. Peptide Sci.*, 1995, 3, 175–183.

Cundliffe, E., "Recognition Sites for Antibiotics within rRNA", Chapter 41, *The Ribosome*, Hill et al. eds., 1989, Am. Soc. Microbiol., Washington, D.C., 479–490.

Demidov, V.V. et al., "Stability of peptide nucleic acids in human serum and cellular extracts", *Biochem. Pharmacol.*, 1994, 48, 1309–1313.

Dueholm, K.L. et al., "Peptide Nucelic Acid (PNA) with a Chiral Backbone Based on Alanine", *Bioorg. & Med. Chem. Letts.*, 1994, 4, 1077–1080.

Eckhardt, H., "Blocking of the Intiation of Protein Biosynthesis by a Pentanucleotide Complementary to the 3' End of *Escherichia coli* 16 S rRNA", *J. Biol. Chem.*, 1979, 254, 11185–11188.

Egholm, M. et al., "Efficient pH–independent sequence–specific DNA binding by pseudoisocytosine–containing bis–PNA", *Nucl. Acids Res.*, 1995, 23, 217–222.

Egholm, P.E. et al., "Sequence–Selective Recognition of DNA by Strand Displacement with a Thymine–Substituted Polyamide", *Science*, 1991, 254, 1497–1500.

Egholm, M. et al., "Peptide Nucleic Acids (PNA). Oligonucleotide Analogues with an Achiral Peptide Backbone", *J. Am. Chem. Soc.*, 1992, 114, 1895–1897.

Egholm, M. et al., "Recognition of Guanine and Adenine in DNA by Cytosine and Thymine Containing Peptide Nucleic Acids (PNA)", *J. Am. Chem. Soc.*, 1992, 114, 9677–9678.

Egholm, M. et al., "Peptide Nucleic Acids containing Adenine or Guanine recognize Thymine and Cytosine in Complementary DNA Sequences", *J. Chem. Soc. Chem. Commun.*, 1993, 800–801.

Egholm, M. et al., PNA hybridizes to complementary oligonucleotides obeying the Watson–Crick hydrogen–bonding rules, *Nature*, 1993, 365, 566–568.

Ellman, J. et al., "Biosynthetic Method for Introducing Unnatural Amino Acids Site–Specifically into Proteins", *Methods in Enzymol.*, 1991, 202, 301–337.

Engberg, J. et al., "Structural Map of 23S rRNA", Chapter 11, *The Ribosome*, Hill et al. eds., 1989, Am. Soc. Microbiol., Washington, D.C., 168–179.

Fissekis, J.D. et al., "Synthesis of 5–Carboxymethyluridine. A Nucleoside from Transfer Ribonucleic Acid", *Biochemistry*, 1970, 9, 3163–3142.

Hanvey, J.C. et al., "Antisense and Antigene Properties of Peptide Nucelic Acids", *Science*, 1992, 258, 1481–1485.

Helene, C. et al., "Specific regulation of gene expression of antisense, sense and antigene nucleic acids", *Biochim. Biophys. Acta.*, 1990, 1049, 99–125.

Hill, W.E., "Probing Ribosome Structure and Function by Using Short Complementary DNA Oligomers", Chapter 18, *The Ribosome*, Hill et al. eds., 1989, Am. Soc. Microbiol., Washington, D.C., 253–261.

Hyrrup, B. et al., "Modification of the Binding Affintity of Peptide Nucleic Acids (PNA). PNA with Extended Backbones consisting of 2–Aminoethyl–β–alanine or 3–Aminopropylglycine Units", *J. Chem. Soc. Chem. Commun.*, 1993, 518–519.

Impacts of Antibiotic–Resistant Bacteria, Sep. 1995, OTA–H–629, GPO stock #052–003–001446–7, pp. 1–8.

(List continued on next page.)

Primary Examiner—Ardin H. Marschel
(74) *Attorney, Agent, or Firm*—Woodcock Washburn Kurtz Mackiewicz & Norris LLP

(57) ABSTRACT

Methods of and compositions for killing or inhibiting the growth of a bacteria are disclosed. The methods comprise the use of peptide nucleic acid that is targeted to mRNA and/or rRNA. In certain embodiments, methods include the use of one or more separate antibiotics.

13 Claims, No Drawings

OTHER PUBLICATIONS

Jarayaraman, K. et al., "Selective inhibition of *Escherichia coli* protein synthesis and growth by nonionic oligonucleotides complementary to the 3' end of 16S rRNA", *Proc. Natl. Acad. Sci.*, 1981, 78, 1537–1541.

Kingman, S., "Resistance a European Problem, Too", *Science*, 1994, 264, 363–365.

Knudsen, H. et al., "Antisense properties of duplex–and triplex–forming PNAs", *Nuc. Acids Res.*, 1996, 24, 494–500.

Kobayashi, S. et al., "Simple Assay of β–Lactamase with Agar Medium Containing a Chromogenic Cephalosporin, Pyridinium–2–Azo–p–Dimethylanilene Chromphore (PADAC)", *Antimicrob. Agents Chemotherapy*, 1988, 32, 1040–1045.

Korobkova, E.S., et al., *Mikrobiol. Z.*, 1995, 57, 30–36.

Lagriffoul, P.H. et al., "The Synthesis, Co–Oligomerization and Hybridization of a Thymine–Thymine Heterodimer Containing PNA", *Bioorg. Med. Chem. Letts.*, 1994, 4, 1081–1082.

Meyer, H.A. et al., "Effects of antisense DNA against the α–sarcin stem–loop structure of the ribosomal 23S rRNA", *Nucl. Acids Res.*, 1996, 24 3996–4002.

Miller, J.H., "Assay of β–Galactosidase", *Experiments in Molecular Genetics*, 1972, Cold Spring Harbor, New York, 352–355.

Miller, J.H., "Episome Transfers: Direct Selection", *Experiments in Molecular Genetics*, 1972, Cold Spring Harbor, New York, 82–85.

Nielsen, P.E. et al, "Sequence specific inhibition of DNA restriction enzyme cleavage by PNA", *Nuc. Acids. Res.*, 1993, 21, 197–200.

Nielsen, P.E. et al., "Sequence–specific transcription arrest by peptide nucleic acid bound to the DNA template strand", *Gene*, 1994, 149, 139–145.

Noller, H.F. et al., "Unusual Resistance of Peptidyl Transferase to Protein Extraction Procedures", *Science*, 1992, 256, 1416–1419.

Norton, J.C. et al., "Inhibition of human telomerase activity by peptide nucleic acids", *Nature Biotechnology*, 1996, 14, 615–619.

Rahman, M.A. et al., "Antibacterial Activity and Inhibition of Protein Synthesis in *Escherichia coli* by antisense DNA Analogs", *Antisense Research and Development*, 1991, 1, 319–327.

Sampson, B.A. et al., "Identification and Characterization of a New Gene of *Escherichia coli* K–12 Involved in Outer Membrane Permeability", *Genetics*, 1989, 122, 491–501.

Saxena, S.K. et al., "Microinjected Oligonucleotides Complementary to the α–Sarcin Loop of 28 S RNA Abolish Protein Synthesis in Xenopus Oocytes", *J. Boil. Chem.*, 1990, 265, 3263–3269.

Sekiguchi, M. et al., "Mutants of *Escherichia coli* Pemeable to Actinomycin", *Proc. Nat. Acad. Sci.*, 1967, 58, 2315–2320.

Sharma, H.W., Naryanan, R., "The therapeutic potential of antisense oligonucleotides", *BioEssays*, 1995, 17, 1055–1063.

Sorensen, M.A. et al., "Codon Usage Determines Translation Rate in *Escherichia coli*", *J. Mol. Biol.*, 1989, 207, 365–377.

Steitz, J.A., Jakes, K., "How ribosomes select initiator regions in mRNA: Base pair formation between the 3' terminus of 16S rRNA and the mRNA during initiation of protein synthesis in *Escherichia coli*", *Proc. Natl. Acad. Sci.*, 1975, 72, 4634–4738.

Taniguchi, T. et al., "Inhibition of Qβ RNA 70S ribosome initiation complex formation by an oligonucleotide complementary to the 3' terminal region of *E. coli* 16S ribosomal RNA", *Nature*, 1978, 275, 770–772.

Travis, J., "Reviving the Antibiotic Miracle?", *Science*, 1994, 264, 360–362.

Uhlmann, E,. et al., "Antisense Oligonucleotides: A New Therapeutic Principle", *A. Chem. Rev.*, 1990, 90, 544–584.

Walker, K., et al., "Inhibition of Protein Synthesis by Anti–5.8S rRNA Oligodeoxyribonucleotides", *J. Biol. Chem.*, 1990, 265, 2428–2430.

Wren, B.W. et al., "A PCR–Based Strategy for the Rapid Construction of Defined Bacterial Deletion Mutants", *BioTechniques*, 1994, 16, 994–996.

ANTIBACTERIAL AND ANTIBIOTIC METHODS USING PEPTIDE NUCLEIC ACIDS AND PHARMACEUTICAL COMPOSITIONS THEREFOR

FIELD OF THE INVENTION

The present invention is directed to peptide nucleic acids and to methods of inhibiting bacterial growth and/or bacterial gene expression using peptide nucleic acids.

BACKGROUND OF THE INVENTION

From the discovery of penicillin by Fleming in 1940's there has been a constant search for new antibiotics, which search continues to this day. Although many antibiotics have been discovered, there is an on-going need for the discovery of new antibiotic compounds because of the emergence of drug resistant strains of bacteria. Thus, research on bacterial infection is a perpetual cycle of development of new antibiotics. When penicillin was first discovered, its broad-spectrum antibiotic activity was hailed as the "magic bullet" in fighting many bacterial infections. However, over the years, many strains of bacteria have developed a resistance to penicillin and other currently available antibiotic drugs. No antibiotic drug is effective against all bacterial infections. Many antibiotic drugs available today have narrow-spectrum of activity, that is, they are effective against only few specific types of bacterial infections. Thus, for example, the majority of current antibiotic drugs are ineffective against syphilis and tuberculosis. In addition, some strains of syphilis, tuberculosis and other bacteria have developed resistance to currently available antibiotic drugs, which were effective drugs in the past.

Oligonucleotides and their analogs have been developed and used in molecular biology in certain procedures as probes, primers, linkers, adapters, and gene fragments. Modifications to oligonucleotides used in these procedures include labeling with non isotopic labels, e.g. fluorescein, biotin, digoxigenin, alkaline phosphatase, or other reporter molecules.

Other modifications have been made to the ribose phosphate backbone to increase the nuclease stability of the resulting analog. These modifications include use of methyl phosphonates, phosphorothioates, phosphorodithioate linkages, and 2'-O-methyl ribose sugar units. Further modifications, include modifications made to modulate uptake and cellular distribution. Phosphorothioate oligo-nucleotides are presently being used as antisense agents in human clinical trials for various disease states including use as antiviral agents. With the success of these oligonucle-otides for both diagnostic and therapeutic uses, there exists an ongoing demand for improved oligonucleotide analogs.

Oligonucleotides can interact with native DNA and RNA in several ways. One of these is duplex formation between an oligonucleotide and a single stranded nucleic acid. The other is triplex formation between an oligonucleotide and double stranded DNA to form a triplex structure.

Peptide nucleic acids are compounds that in certain respects are similar to oligonucleotide analogs however in other very important respects their structure is very different. In peptide nucleic acids, the deoxyribose backbone of oli-gonucleotides has been replaced with a backbone more akin to a peptide than a sugar. Each subunit, or monomer, has a naturally occurring or non naturally occurring base attached to this backbone. One such backbone is constructed of repeating units of N-(2-aminoethyl)glycine linked through amide bonds. Because of the radical deviation from the deoxyribose backbone, these compounds were named peptide nucleic acids (PNAs).

PNA binds both DNA and RNA to form PNA/DNA or PNA/RNA duplexes. The resulting PNA/DNA or PNA/RNA duplexes are bound with greater affinity than corresponding DNA/DNA or DNA/RNA duplexes as determined by Tm's. This high thermal stability might be attributed to the lack of charge repulsion due to the neutral backbone in PNA. The neutral backbone of the PNA also results in the Tm's of PNA/DNA(RNA) duplex being practically independent of the salt concentration. Thus the PNA/DNA duplex interaction offers a further advantage over DNA/DNA duplex interactions which are highly dependent on ionic strength. Homopyrimidine PNAs have been shown to bind complementary DNA or RNA forming (PNA)2/DNA(RNA) triplexes of high thermal stability (see, e.g., Egholm, et al., Science, 1991, 254, 1497; Egholm, et al., J. Am. Chem. Soc., 1992, 114, 1895; Egholm, et al., J. Am. Chem. Soc., 1992, 114, 9677).

In addition to increased affinity, PNA has also been shown to bind to DNA with increased specificity. When a PNA/DNA duplex mismatch is melted relative to the DNA/DNA duplex there is seen an 8 to 20° C. drop in the Tm. This magnitude of a drop in Tm is not seen with the corresponding DNA/DNA duplex with a mismatch present.

The binding of a PNA strand to a DNA or RNA strand can occur in one of two orientations. The orientation is said to be anti-parallel when the DNA or RNA strand in a 5' to 3' orientation binds to the complementary PNA strand such that the carboxyl end of the PNA is directed towards the 5' end of the DNA or RNA and amino end of the PNA is directed towards the 3' end of the DNA or RNA. In the parallel orientation the carboxyl end and amino end of the PNA are just the reverse with respect to the 5'-3' direction of the DNA or RNA.

PNAs bind to both single stranded DNA and double stranded DNA. As noted above, in binding to double stranded DNA it has been observed that two strands of PNA can bind to the DNA. While PNA/DNA duplexes are stable in the antiparallel configuration, it was previously believed that the parallel orientation is preferred for $(PNA)_2$/DNA triplexes.

The binding of two single stranded pyrimidine PNAs to a double stranded DNA has been shown to take place via strand displacement, rather than conventional triple helix formation as observed with triplexing oligonucleotides. When PNAs strand invade double stranded DNA, one strand of the DNA is displaced and forms a loop on the side of the $PNA_2$/DNA complex area. The other strand of the DNA is locked up in the $(PNA)_2$/DNA triplex structure. The loop area (alternately referenced as a D loop) being single stranded, is susceptible to cleavage by enzymes that can cleave single stranded DNA.

A further advantage of PNA compared to oligonucleotides is that their polyamide backbones (having appropriate nucleobases or other side chain groups attached thereto) is not recognized by either nucleases or proteases and are not cleaved. As a result PNAs are resistant to degradation by enzymes unlike nucleic acids and peptides.

Because of their properties, PNAs are known to be useful in a number of different areas. Since PNAs have stronger binding and greater specificity than oligonucleotides, they are used as probes in cloning, blotting procedures, and in applications such as fluorescence in situ hybridization (FISH). Homopyrimidine PNAs are used for strand displacement in homopurine targets. The restriction sites that overlap with or are adjacent to the P-loop will not be cleaved by restriction enzymes. Also, the local triplex inhibits gene transcription. Thus in binding of PNAs to specific restriction sites within a DNA fragment, cleavage at those sites can be inhibited. Advantage can be taken of this in cloning and subcloning procedures. Labeled PNAs are also used to directly map DNA molecules. In effecting this, PNA molecules having a fluorescent label are hybridized to complementary sequences in duplex DNA using strand invasion.

PNAs have further been used to detect point mutations in PCR-based assays (PCR clamping). PCR clamping uses PNA to detect point mutations in a PCR-based assay, e.g. the distinction between a common wild type allele and a mutant allele, in a segment of DNA under investigation. A PNA oligomer complementary to the wild type sequence is synthesized. The PCR reaction mixture contains this PNA and two DNA primers, one of which is complementary to the mutant sequence. The wild type PNA oligomer and the DNA primer compete for hybridization to the target. Hybridization of the DNA primer and subsequent amplification will only occur if the target is a mutant allele. With this method, one can determine the presence and exact identity of a mutant.

Considerable research is being directed to the application of oligonucleotides and oligonucleotide analogs that bind complementary DNA and RNA strands for use as diagnostics, research reagents and potential therapeutics. PCT/EP/01219 describes novel peptide nucleic acid (PNA) compounds which bind complementary DNA and RNA more tightly than the corresponding DNA. Because of these binding properties as well as their stability, such PNA compounds find many uses in diagnostics and research reagents uses associated with both DNA and RNA. With complementary DNA and RNA they can form doublestranded, helical structures mimicking doublestranded DNA, and they are capable of being derivatized to bear pendant groups to further enhance or modulate their binding, cellular uptake, or other activity.

Specific sequence recognition of DNA or RNA is of increasing importance for the development of biological probes and new reagents for use in research (Uhlmann, E., Peyman, A., *Chem. Rev.,* 1990, 90, 544, and Helene, C., Toulme, J. J., *Biochim. Biophys. Acta.,* 1990, 1049, 99). Peptide nucleic acid (PNA), have properties making them well suited for use as biological probes and other applications. PNA have shown strong binding affinity and specificity to complementary DNA, sequence specific inhibition of DNA restriction enzyme cleavage and site specific in vitro inhibition of translation (Egholm, M., et al., *Chem. Soc., Chem. Commun.,* 1993, 800; Egholm, M., et. al., *Nature,* 1993, 365, 566; and Nielsen, P., et. al. *Nucl. Acids Res.,* 1993, 21, 197). Furthermore, PNA's show nuclease resistance and stability in cell-extracts (Demidov, V. V., et al., *Biochem. Pharmacol.,* 1994, 48, 1309–1313). Modifications of PNA include extended backbones (Hyrup, B., et. al. *Chem. Soc., Chem. Commun.,* 1993, 518), extended linkers between the backbone and the nucleobase, reversal of the amido bond (Lagriffoul, P. H., et. al., *Biomed. Chem. Lett.,* 1994, 4, 1081), and the use of a chiral backbone based on alanine (Dueholm, K. L, et. al., *BioMed. Chem. Lett.,* 1994, 4, 1077).

A method of inhibiting protein synthesis by contacting 28S rRNA of a protein synthesizing system with a protein synthesis inhibitory amount of an oligonucleotide that hybridizes to the sarcin recognition domain loop of the 28S rRNA has been previously reported (U.S. Pat. No. 5,220, 014, entitled rRNA Specific Oligonucleotides, issued Jun. 15, 1993).

Antibacterial activity and inhibition of protein synthesis in *E. coli* has been reported using DNA analogs having methylcarbonate internucleoside linkages in place of phosphodiester linkages (Rahman, M. A., et al., *Antisense Research and Development,* 1991, 1, 319–327).

The 3' end of the 16S rRNA of *E. coli* has been targeted by a complementary pentanucleotide. The initiation of protein biosynthesis is thereby blocked (Eckhardt, H., Luhrmann, R., *J. Biol. Chem.,* 1979, 254, 11185–11188).

Selective inhibition of *E. coli* protein synthesis and growth by nonionic oligonucleotides (methylphosphonate linkages) complementary to the 3' end of the 16S rRNA has been previously reported (Jayaraman, K., et al., *Proc. Natl. Acad. Sci.,* 1981, 78, 1537–1541).

Oligodeoxyribonucleotides complementary to the 3' terminal segment of the 16s-rRNA in molecules have shown suppression of translation in their ribosomes in an in-vitro assay (Korobkova, E. S., et al., *Mikrobiol. Z.,* 1995, 57, 30–36).

Peptide Nucleic Acids are described in U.S. Pat. No. 5,539,082, issued Jul. 23, 1996, entitled Novel Peptide Nucleic Acids and U.S. Pat. No. 5,539,083, issued Jul. 23, 1996, entitled PNA Combinatorial Libraries and Improved Methods of Synthesis, the contents of which are hereby incorporated by reference. Peptide Nucleic Acids are further described in U.S. patent application, Ser. No. 08/686,113, filed Jul. 24, 1996, entitled Peptide Nucleic Acids Having Enhanced Binding Affinity and Sequence Specificity, in which a supplemental notice of allowability dated Jun. 2, 1997, has been received, the contents of which is hereby incorporated by reference.

SUMMARY OF THE INVENTION

One aspect of the present invention provides methods of killing or inhibiting growth of a bacteria comprising contacting the bacteria with a peptide nucleic acid. The methods include employment of peptide nucleic acid that is complementary to a region of the bacteria ribosomal RNA. The methods further include use of peptide nucleic acid that is complementary to a region of the bacteria messenger RNA. In one aspect of the invention, the methods include contacting the bacteria with at least one PNA or PNA-linked antibiotic. In one embodiment of the invention, peptide nucleic acids are from 5 to about 40 monomer units in length. In a preferred embodiment of the invention peptide nucleic acids are from about 5 to about 25 monomer units in length.

In a further aspect of the invention, the methods include peptide nucleic acid complementary to a region of the bacteria ribosomal RNA and a further peptide nucleic acid complementary to a region of the bacteria messenger RNA. The use of peptide nucleic acid to both ribosomal RNA and messenger RNA may further include at least one antibiotic.

A further aspect of the present invention provides an antibacterial composition comprising a peptide nucleic acid. In one embodiment the composition includes a further peptide nucleic acid. In a preferred embodiment the peptide nucleic acid has bacteriostatic or bacteriocidal properties. In one embodiment the peptide nucleic acid is targeted to an essential bacterial gene.

In another aspect, the present invention provides antibacterial pharmaceutical compositions comprising peptide nucleic acid. In one embodiment the peptide nucleic acid is targeted to an essential bacterial gene. In a preferred embodiment the targeted gene is encodes β-lactamase. In a more preferred embodiment the antibacterial pharmaceutical composition further comprises a β-lactam antibacterial agent.

The present invention further provides methods of treating a subject suffering from a bacterial infection by administration of a peptide nucleic acid. In one embodiment the method includes a peptide nucleic acid complementary to a region of the bacteria ribosomal RNA. In another embodiment the method includes a peptide nucleic acid complementary to a region of the bacteria mRNA. A further embodiment includes concurrent treatment with an antibiotic.

The present invention includes methods of disinfection comprising selecting an object to be disinfected and contacting the object with peptide nucleic acid. The peptide nucleic is removed by rinsing the object with a sterile liquid to remove the peptide nucleic acid. In a preferred embodiment, the peptide nucleic acid is in a solution and the object is contacted with the solution over all solvent accessible areas of the object.

DETAILED DESCRIPTION OF THE INVENTION

The present invention relates to methods of killing or inhibiting the growth of bacteria through treatment with either PNAs alone or PNAs in combination with one or more antibiotics. rRNA targeted PNAs alone have bactericidal or growth inhibitory effects on selected bacteria. mRNA targeted PNAs alone are effective in selectively blocking production of selected proteins. mRNA targeted PNAs can be used to enhance the effects of selected antibiotics by targeting genes responsible for the production of proteins that inhibit the activity of the antibiotic. In a multi-drug approach, rRNA targeted PNAs, mRNA targeted PNAs and selected antibiotics can be used simultaneously to give a synergistic effect.

In one aspect of the present invention rRNA of E. coli is targeted by selected PNAs. rRNA is essential for the translation of mRNA in the production of proteins and has been reported to be a preferred target of inhibition of translation (Noller, H. F., et al., Science, 1992, 256, 1416–1419). There are a number of natural antibiotics that appear to act by binding to rRNA (Cundliff, E., (1989). In the Ribosome, Hill, et al., Eds., Am. Soc. Microbiol., Washington, D.C., 479–490).

The binding of a PNA strand to a DNA or RNA strand can occur in one of two orientations. The orientation is said to be anti-parallel when the DNA or RNA strand in a 5' to 3' orientation binds to the complementary PNA strand such that the carboxyl end of the PNA is directed towards the 5' end of the DNA or RNA and amino end of the PNA is directed towards the 3' end of the DNA or RNA. In the parallel orientation the carboxyl end and amino end of the PNA are just the reverse with respect to the 5'-3' direction of the DNA or RNA.

In accordance with this invention, it has now been found that very stable triplexes are formed between two single stranded PNAs or a linked PNA (bis PNA) and a mRNA or rRNA target strand where the Watson/Crick base pairing strand is in an anti-parallel orientation relative to the target strand and the Hoogsteen base pairing strand is in a parallel orientation relative to the target strand. As so orientated to the target strand, the two PNA strands are therefore anti-parallel to each other. Such stability is very desirable.

In the Hoogsteen strand of the linked PNAs the cytosines have been replaced with pseudo isocytosines. Normal Hoogsteen binding requires that the cytosines be protonated. This makes the Hoogsteen strand binding pH dependent. We have previously found that replacement of one or more of the cytosine nucleobases in a Hoogsteen strand with pseudo isocytosine and other like nucleobases removes this dependence. The replacement of cytosine by pseudo isocytosine or other like C-pyrimidine nucleobases is effected in a straight forward manner as illustrated in the examples below.

Duplex and triplex forming PNAs were synthesized to anneal to the RNA component of the E. coli ribosome. The selected target regions of the rRNA was within the peptidyl transferase center, the α-sarcin loop and the mRNA binding domain at the 3' end of the 16S rRNA. These sites are functionally active and appear to be accessible for interactions with antibiotics, translation factors, structure probing agents, other RNA molecules and short oligonucleotides (Steitz, J. A., Jakes, K., PNAS, 1975, 72, 4634–4738; Engberg, J., et al., (1989), In the Ribosome, Hill, et al., Eds., Am. Soc. Microbiol., Washington, D.C., 168–179; Hill, W. E., (1989), In the Ribosome, Hill, et al., Eds., Am. Soc. Microbiol., Washington, D.C., 253–261). The inhibition of rRNA in vitro by DNA oligonucleotides has been shown in previous studies (Taniguchi, T., Weissmann, C., Nature, 1978, 275, 770–772; Walker, K., et al., J. Biol. Chem., 1989, 265, 2428–2430; Saxena, S. K., Ackerman, E. J., J. Boil. Chem., 19909, 265, 3263–3269; Brigotti, M., et al., Biochem. Mol. Biol. Int., 1993, 31, 897–903; Meyer, H. A., et al., Nucl. Acids Res., 1996, 24, 3996–4002). It has also been shown that PNA targeted to template RNA within telomerase can inhibit its enzymatic activity (Norton, J. C., et al., Nature Biotechnology, 1996, 14, 615–619). Superior hybridization and stability of PNAs have been previously demonstrated via the blocking of polymerase and ribosome progression when bound to template sequences (Hanvey, J. C., et al., science, 1992, 258, 1481–1485; Nielsen, P. E., et al., gene, 1994, 149, 139–145; Knudsen, H., Nielsen, P. E., Nucl. Acids Res., 1996, 24, 494–500).

While not wanting to be bound by theory, it is believed that the PNAs targeted to rRNA effect killing or inhibition of bacterial growth by effecting gene expression at the level of translation. Supportive of this reasoning are examples 5–8 below. In identical in-vitro assays the inhibition of protein synthesis is determined first by calorimetric measurement of protein synthesis and second by measurement of radioactive methionine and UTP incorporated into protein and mRNA respectively. After the inhibition of β-galactosidase synthesis was determined calorimetrically (Example 5) the assay was rerun using $^{32}$P-UTP and $^{35}$S-methionine (Example 6). The level of radioactive methionine incorporation decreased while the level of radioactive UTP remained constant with increasing amounts of rRNA targeted PNA added to the assay. The data show uninterrupted transcription with a steady decrease in translation.

In another aspect of the present invention, methods of killing or inhibiting the growth of a bacteria are effected through the use of PNAs targeted to mRNA. The advantage to using mRNA targeted PNAs is that only specific gene products need be targeted. mRNA targeted PNAs can be targeted to core proteins necessary for the survival and replication of bacterial cells thereby inhibiting cell growth. PNAs can also be targeted to specific mRNAs that are responsible for the synthesis of proteins that for example inhibit the effects of particular antibiotics. In other aspects, solutions of PNAs can be used to disinfect objects that have been contaminated with a particular bacteria. The disinfection procedure can designed in a specific manner thereby affecting only the bacteria that is undesired leaving other bacteria or microorganisms unaffected.

Studies using PNAs targeted to the start codon regions of β-galactosidase and β-lactamase genes of E. coli showed inhibitory effects both in-vitro and in-vivo. The start codon has been suggested as a viable target for antisense oligonucleotides (Sharma, H. W., Narayanan, R., BioEssays, 1995, 17, 1055–1063). In in-vitro studies the targeted PNAs showed activity and specificity. The activity was limited to the target gene mRNA and had no effect on non-targeted mRNA as seen by assays measuring protein production (Examples 1 and 2). The same study was repeated using the intact gene in comparison with two mutant genes. The activity was greatly reduced when the gene had 2 non-essential base substitutions. There was no activity observed when the mutant gene had 6 non-essential base substitutions.

UTILITY OF THE INVENTION

Most bacteria which are resistant to a given drug also exhibit similar resistance to chemically similar drugs. Currently, many antibiotics are based on the β-lactam chemical core structure of penicillin. Although other chemically diverse antibiotics, such as vancomycin, are currently available, it is only a matter of time before the emergence of bacterial strains which will be resistant to all currently available antibiotic drugs. Thus, to prevent a future worldwide epidemic of drug resistant bacterial infections, there is a never ending need for a development of antibiotic drugs with novel chemical structures (Travis, J., Science, 1994, 264, 360–362; Kingman, S., Science, 1994, 264, 363–365; and Impacts of Antibiotic-Resistant Bacteria, September, 1995, OTA-H-629, GPO stock #052-003001446-7, pages 1–8). This invention addresses this goal and many others as detailed below.

Moreover, the methods and compositions of the invention provide for control of gene expression in bacteria. When targeted to an essential gene, such as that encoding DNA Gyrase, DNA Polymerase, RNA Transcriptase, etc. (cite), the methods and compositions of the invention provide for bacteriostatic and/or bacteriocidal means for carrying out antibacterial modes of the invention.

The methods and compositions of the invention provide for an antibacterial composition comprising a peptide nucleic acid that can be used for, e.g., a disinfectant. The antibacterial compositions of the invention have bacteriostatic and/or bacteriocidal properties. In one embodiment, such antibacterial compositions comprise a peptide nucleic acid targeted to an essential bacterial nucleic acid such as, for example, a ribosomal RNA (rRNA).

The antibacterial compositions of the invention can, according the methods of the invention, be used to disinfect objects desired to be disinfected by contacting them with antibacterial compositions of the invention. Such objects to be disinfected can be composed of a number of materials (e.g., polished metals, durable plastics and the like) and include, but are not limited to, physician's tools, including many tools used in examination rooms and more specifically, surgical tools and instruments, such as scalpels and scissors and the like; and barber's and beauticians's tools, such as combs, razors, and the like.

Furthermore, the compositions of the invention can be used to form antibacterial pharmaceutical compositions comprising either a PNA of the invention or such a PNA in combination with one or more other antibacterial agents. Such antibacterial pharmaceutical compositions include one or more PNAs targeted to bacterial genes or RNAs, including genes encoding DNA Gyrase, DNA Polymerase, Transcriptase, etc. In one particularly favored embodiment, the PNAs of the method targeted a gene to b-lactamase are combined with one or more b-lactam agents having antibacterial activity, e.g., penicillin, amoxocillin and the like.

The following examples are merely illustrative of the present invention and should not be considered limiting of the scope of the invention in any way. These examples and equivalents thereof will become more apparent to those skilled in the art in light of the present disclosure and the accompanying claims. The disclosures of each patent, patent application, and publication cited or described in this document are hereby incorporated herein by reference in their entirety.

EXAMPLE 1

PNAS, Bacterial Strains and Assays of the Invention

A. Peptide Nucleic Acids (PNAS)

The PNAs used for the study were synthesized as per Christensen, L., ibid, and Egholm, M., et al., Nucl. Acids Res., 1995, 23, 217–222; and Christensen, L., et al., J. Peptide Sci., 1995, 3, 175–183.

Sequences and corresponding SEQ ID NOS: used in the Examples are shown in Table 1 below:

TABLE 1

| Sequences of PNA targeted to β-Galactosidase (start codon region) | |
|---|---|
| SEQ ID NO: | PNA-SEQUENCE |
| 5 | H-GGT CAT AGC TGT TTC-Lys-$NH_2$ |
| 6 | H-TAC TCA TAC TCT TCC-Lys-$NH_2$ |
| 7 | H-GAA TAC TCA TAC TCT-Lys-$NH_2$ |
| 8 | H-ACG CCA CAT CTT CGC-Lys-$NH_2$ |

B. Bacterial Strains

The E. coli strains K12 (wildtype) and D10(rna-10) were from the E. coli genetic stock center(Yale University). The permeable strain AS19 (Sekiguchi, ibid.) was obtained from the University of Copenhagen (Steen Pedersen). A derivative of D10(d10-1) containing the lacIq gene for repressor overproduction was constructed by transfer of the F' factor from strain JM101 as described in Miller, J. H., Experiments in Molecular Genetics, 1972, Cold Spring Harbor, N.Y., 1972, 352–355. The permeable strain AS19 (Sekiguchi, M., et al., PNAS, 1967, 58, 2315–1220) was obtained from S. Pedersen (University of Copenhagen).

C. Plasmids

The wildtype β-galactosidase gene carried in pMAS2 was obtained from M. A. Sorensen, University of Copenhagen (see Sorensen, M. A., et al., J. Mol. Biol., 1989, 207, 365–377). The transposon Tn3 β-lactamase gene, was used in its wild-type form as carried in pBR322 and base changes in the start codon region were introduced by inverse PCR mutagenesis as described previously (Wren, B. W., et al., Biotechniques, 1994, 16, 994–996), using the primers TGA CCA TGA TTA CG (SEQ ID NO: 1) and TAC GTG TTT CCT GTG TG (SEQ ID NO: 2) to create pLac-2 and the primers GAG TAT TCA ACA TTT CC (SEQ ID NO: 3) and ATT GTC TTC CTT TTT CA (SEQ ID NO: 4) to create pLac-6.

D. Assays

1. Enzymatic assays

To assay the inhibition of β-lactamase, cultures (100 mL) were initiated with 1% (vol/vol) of an overnight E. coli culture in microfuge tubes (1.5 mL) containing PNA. The cultures were grown at 37° C. to approximately 0.5 O.D. 550 nm. β-Lactamase activity was determined using the chromogenic β-lactamase substrate PADAC (Calbiochem, San Diego, Calif.) and absorbance measurements at 570 nm (Kobayashi, et al., *Antimicrob. Agents Chemotherap.,* 1988, 32, 1040). β-Galactosidase activity was determined using the substrate o-nitrophenyl-β-galactoside (ONPG) and absorbance measurements at 420 nm as described previously (Miller, J. H., Experiments in *Molecular Genetics,* 1972, Cold Spring Harbor, N.Y., 1972, 82–85).

2. In vitro Assays (S-30 extracts)

Strain D10-1 was grown to mid log phase in LB media supplemented with 4 g/L glucose. The preparation of S-30 cell extracts and coupled transcription/translation reactions were carried out as described in Ellman, J., ibid., using plasmid pMAS2, which carries the *E. coli* gene for β-galactosidase. The reaction components were aliquoted into microfuge tubes on ice to a total volume of 30 μL, vortexed briefly and incubated at 37° C. for 30 minutes. β-galactosidase activity was measured using the substrate o-nitrophenyl-β-galactoside (ONPG) and absorbance measurements at 420 nm as described in Miller, ibid.

Transcription in the cell-free system was assayed using reactions that contained 34 μM of cold UTP and 1 μCi $^{32}$P-UTP. After 30 minutes the reactions were stopped with 10 volumes of 5% TCA and incubated on ice for 30 minutes. Translation in the cell-free system was assayed using reactions that contained 5 mM cold UTP and 1 μCi $^{35}$S-methionine. After 30 minutes the reactions were stopped with an equal volume of 1 M NaOH and placed at 37° C. for 15 minutes. An equal volume of cold 50% TCA containing 2% casein hydrolysate acids was added and after 30 minutes on ice, 1 mL of 5% TCA was added. The TCA precipitable material having radioactivity was collected by vacuum filtration, rinsed five times with 5% TCA and dried. Cerenkov and scintillation counting were used to determine $^{32}$P-UTP and $^{35}$S-methionine incorporation.

antibiotic solutions and the plates were incubated overnight at 37° C. The presence or absence of growth was assessed visually as a zone of clearing on solid media or as a lack of turbidity in liquid cultures.

EXAMPLE 2

Determination of in-vitro Activity

PNA oligomers (SEQ ID NOs. 5–8 above) were evaluated in an in-vitro assay in which plasmid DNA encoding the genes for β-galactosidase and β-lactamase were added to a template depleted *E. coli* S-30 cell extract along with the reagents necessary for coupled transcription and translation (Chen, H. Z., Zubay, G., *Methods in Enzymol.,* 1983, 101, 674–690; Ellman, J., et al., *Methods in Enzymol.,* 1991, 202, 301–337). The assay is sensitive to inhibitors that prevent initiation of translation. The antisense PNAs specifically inhibited enzyme production from targeted mRNA in a dose dependent manner. The PNA concentrations required for a 50% inhibition (IC$_{50}$) of activity were 10 nM for SEQ ID NO: 5 targeted to the β-galactosidase, 30 nM for SEQ ID NO: 6 targeted to β-lactamase and 200 nm for SEQ ID NO: 7 also targeted to β-lactamase. The control PNA (SEQ ID NO: 8) having an unrelated sequence relative to the targets showed no inhibition at concentrations as high as 400 nM. Active PNAs showed no effect on the non-targeted gene in the assays performed. The results show that the antisense effects are gene specific and not due to a general reduction in transcription or translation in the cell-free system.

The specificity of PNAs SEQ ID NOs. 6 and 7 for two β-lactamase gene mutants was determined by repeating the above procedure with the following changes. One of the β-lactamase gene mutants contained 2 non-essential base substitutions (pLac-2) and the other of the genes contained 6 non-essential base substitutions (pLac-6) as shown below:

```
5'-AA AGG AAG AGU AUG AGU AUU CAA CAU U-3' unmodified    SEQ ID NO:21
5'-AA AGG AAG ACA AUG AGU AUU CAA CAU U-3' (pLac-2) SEQ
ID NO:22
5'-AA AGG AGG CCU AUG UCG AUU CAA CAU U-3' (pLac-6) SEQ
ID NO:23
Met. (start codon)
```

3. In vivo Assays

For the in vivo assay of the inhibition of β-galactosidase, *E. coli* strain AS19 was grown to early log phase in Luria Broth (LB) and aliquoted (40 μL) into small volume microfuge-PCR tubes. PNAs were added to the cultures and pre-incubated with the cells for 15 minutes at 37° C. The lac operon was induced with IPTG (100 μM). After 15 minutes of induction at 37° C., the cells were lysed by vortexing with chloroform (5 μL). To assay the inhibition of β-lactamase, cultures (100 mL) were initiated with 1% (vol/vol) of an overnight *E. coli* culture in microfuge tubes (1.5 mL) containing PNA. The cultures were grown at 37° C. to approximately 0.5 O.D. 550 nm.

4. Growth Assays

Growth assays were initiated using Luria Broth (LB) Media inoculated with 1% (v/v) of an overnight *E. coli* culture. For solid media cultures, 2 mL of molten LB/agar media was inoculated and spread onto pre-warmed (LB)/agar plates. The excess molten media was poured off and the plates were left to solidity for 30 minutes. PNA and antibiotic solutions were pipetted (2 μL) directly onto the solidified overlay and the plates were incubated overnight at 37° C. For liquid media cultures, 100 μL of inoculated LB media was aliquoted into microtitre plate wells containing PNA or The IC$_{50}$ for the two PNAs was about 400 nM for pLac-2 which was quite lower than for the unmodified gene. The two PNAs were not able to effect the pLac-6 modified gene. These results show that the observed inhibition involves PNA base pairing to the start codon region.

EXAMPLE 3

Determination of in-vivo Activity

The activity of PNAs in an in-vivo assay was determined. PNA SEQ ID NOs. 5–8 were included in cultures of permeable *E. coli* strain AS19 (Sekiguchi, ibid.) and the expression of β-galactosidase and β-lactamase was measured in cells exposed to IPTG at various time points.

The inhibition of β-galactosidase was measured by incubating cells with PNA for 15 minutes and then inducing the expression of the chromosomal β-galactosidase gene for 15 minutes with IPTG. The inhibition of β-lactamase production was evaluated by growing cells in the presence of PNA from an early stage to mid log phase. In both cases, gene specific and dose dependent inhibition was observed with IC$_{50}$ values in the low micromolar range. No inhibition was observed with the control PNA (SEQ ID NO: 8). It was also observed that the inhibition was gene specific, e.g. only the targeted gene was inhibited.

TABLE 2

IC$_{50}$ values for sequences targeted to β-Galactosidase and β-Lactamase

| SEQ ID NO: | Target | IC$_{50}$(conc.) |
|---|---|---|
| 5 | β-galactosidase | low micromolar range |
| 6 | β-lactamase | low micromolar range |
| 7 | β-lactamase | low micromolar range |
| 8 | control sequence not targeted | no activity measured |

EXAMPLE 4 in-vivo Determination of Specificity

The in-vivo specificity of selected PNAs (SEQ ID NOs. 6 and 7) was determined using *E. coli* AS19 that was transformed with pBR322 and its derivatives containing the target site mutations (pLac-2 and pLac-6). As was found in Example 2, the inhibition of β-lactamase production was reduced in the strain carrying two base substitution and abolished in the strain carrying 6 base substitutions. The results show that the targeted PNAs inhibited enzyme production in vivo by base pairing to the start codon region.

EXAMPLE 5

Cell-free translation Assay

Plasmid DNA encoding β-galactosidase was added to a template depleted *E. coli* S-30 cell extract along with the reagents necessary for coupled transcription/translation (Chen, ibid; Ellman, J., ibid). Production of β-galactosidase was measured calorimetrically using the substrate ONPG (Miller, ibid). The assay is sensitive to inhibitors that prevent complete or accurate translation of the enzyme. Several of the targeted PNAs inhibited β-galactosidase production in a dose dependent manner, with IC$_{50}$s in the nanomolar range. The most potent inhibitors of in vitro protein synthesis were the PNAs targeted to the peptidyl transferase center and the α-sarcin loop (SEQ ID NOs. 12 and 13). The SEQ ID NOs. and the sequences are shown below in Table 2.

TABLE 3

Sequences of PNA Targeted to Ribosomal RNAs

| SEQ ID NO: | PNA-SEQUENCE |
|---|---|
|  | Control PNAs |
|  | triplex forming |
| 9 | H-TJJ JTT J-(egl)$_3$-CTT CCC T-Lys-NH$_2$ |
| 10 | H-JTT TJJ T-(egl)$_3$-TCC TTT C-Lys-NH$_2$ |
|  | duplex forming |
| 11 | H-CAT ACT CTT TCT CCT-Lys-NH$_2$ |
| 5 | H-GGT CAT AGC TGT TTC-Lys-NH$_2$ |
|  | Anti-ribosomal PNAs |
|  | triplex-forming |
| 12 | H-TTJ TJJ JTT TJT-(egl)$_3$-TCT TTC CGT CTT-Lys-NH$_2$ |
| 13 | H-JTJ TJJ T-(egl)$_3$-TCC TCT C-Lys-NH$_2$ |
|  | duplex-forming |
| 14 | H-CCC CTA TTG TCC-LYS-NH$_2$ |
| 15 | H-TTC TGC CTT TCT-Lys-NH$_2$ |
| 16 | H-CTC GAG GT-Lys-NH$_2$ |
| 17 | H-TAA AC-Lys-NH$_2$ |
| 18 | H-AAG GAG GTG A-Lys-NH$_2$ |

(egl = —NH—CH$_2$—CH$_2$—O—CH$_2$—CH$_2$—O—CH$_2$—C(=O)—; J = pseudo isocytosine)

PNAs of similar composition, but unrelated sequence, were assayed along with targeted PNAs as controls for non-sequence specific effects. The IC$_{50}$s for the triplex forming Bis-PNAs (SEQ ID NOs. 12 and 13) was measured as 200 nM and 350 nM respectively. These values are comparable to those obtained from the known translation inhibitor and antibiotic Tetracycline. No inhibition was detected at a dose of 1 μM for the control PNAs. An inhibitory effect of less than 50% was observed for the duplex forming sequences 14 through 18.

EXAMPLE 6

Transcription vs. Translation Assay

The transcription and translation activities yielding β-galactosidase was examined using $^{32}$P-UTP and $^{35}$S- methionine in the assay procedures of Example 5. With increasing concentrations of targeted PNA (SEQ ID NOs. 12 and 13), the level of radioactive methionine incorporation was reduced. The level of radioactive UTP remained the same for all reactions. These data show that the PNA-mediated inhibition of β-galactosidase production occurs at the translation level without significant inhibition of transcription.

EXAMPLE 7

Cell growth Assay using *E. coli* (K12)

The inhibition of cell growth was examined using PNA sequences 9–18 in *E. coli* grown on agar media. Luria broth (LB)/agar plates were prepared with a thin overlay of media containing an inoculum of *E. coli* strain K12. PNA solutions were applied directly onto the solidified overlay by direct pipetting of 2 μL aliquotes. After overnight incubation at 37° C., a lawn of bacterial cells was established. Growth inhibition was evident at sites of application as zones of clearing in the lawn. PNA sequences 12 and 13 inhibited cell growth when applied directly onto solid media cultures. The control PNA sequences showed no inhibitory effects. The duplex forming anti-ribosomal PNAs (SEQ ID NOs. 14–18) showed no effect at concentrations of up to 200 μM. Shifting the binding site or altering the size of duplex forming PNAs may result in increased levels of inhibition in this assay (Norton, J. C., et al., *Nature Biotechnology*, 1996, 14, 615–619).

EXAMPLE 8

Cell growth Assay using *E. coli* (AS19)

A second assay similar to that of Example 7 was performed using *E. coli* mutant strain (AS19). The mutant strain has an increased permeability to many antibiotics (Sekiguchi, ibid.) which influences the action of these drugs (Norton, J. C., et al., *Nature Biotechnology*, 1996, 14, 615–619). PNA SEQ ID NOs. 5 and 9–18 were assayed and the inhibition occurred at about a 10 fold lower concentration than with the K12 strain of *E. coli* . The assay was repeated with the cells in 100 μL liquid cultures. PNA SEQ ID NOs. 12 and 13 showed inhibition at 30 and 10 μM respectively. The inhibition was determined to be that concentration which visibly limited the growth of the *E. coli* in a 100 μL culture.

EXAMPLE 9

N-Benzyloxycarbonyl-N-'(bocaminoethyl)glycine

Aminoethyl glycine (52.86 g; 0.447 mol) was dissolved in water (900 mL) and dioxane (900 mL) was added. The pH was adjusted to 11.2 with 2N NaOH. While the pH was kept at 11.2, tert-butyl-p-nitrophenyl carbonate (128.4 g, 0.537 mol) was dissolved in dioxane (720 mL) and added dropwise over the course of 2 hours. The pH was kept at 11.2 for at least three more hours and then left with stirring overnight. The yellow solution was cooled to 0° C. and the pH was adjusted to 3.5 with 2 N HCl. The mixture was washed with chloroform (4×100 mL), and the pH of the aqueous phase was readjusted to 9.5 with 2 N NaOH at 0° C. Benzyloxycarbonyl chloride (73.5 mL, 0.515 mol) was added over half an hour, while the pH was kept at 9.5 with 2 N NaOH. The pH was adjusted frequently over the next 4 hours, and the solution was left with stirring overnight. On the following day the solution was washed with ether (3×600 mL) and the pH of the solution was afterwards adjusted to 1.5 with 2 N HCl at 0° C. The title compound was isolated by extraction with ethyl acetate (5×1000 mL). The ethyl acetate solution was dried ($MgSO_4$) and evaporated to dryness in vacuo. This afforded 138 g, which was dissolved in ether (300 mL) and precipitated by the addition of petroleum ether (1800 mL). Yield 124.7 g (79%). M.p. 64.5–85° C. Anal. for $C_{17}H_{24}N_2O_6$ found(calc.) C: 58.40 (57.94); H: 7.02(6.86); N: 7.94(7.95). $^1$H-NMR (250 MHZ, $CDCl_3$) 7.33 & 7.32 (5H, Ph); 5.15 & 5.12 (2H, PhC$\underline{H}_2$); 4.03 & 4.01 (2H, NC$\underline{H}_2$CO$_2$H); 3.46 (b, 2H, BocNHCH$_2$C$\underline{H}_2$); 3.28 (b, 2H, BocNHC$\underline{H}_2$CH$_2$); 1.43 & 1.40 (9H, $^t$Bu). HPLC (260 nm) 20.71 minutes (80.2%) and 21.57 minutes (19.8%). The UV-spectra (200 nm–300 nm) are identical, indicating that the minor peak consists of Bis-Z-AEG.

EXAMPLE 10

N'-Boc-aminoethyl glycine ethyl ester

N-Benzyloxycarbonyl-N'-(bocaminoethyl)glycine (60.0 g; 0.170 mol) and N,N-dimethyl-4-aminopyridine (6.00 g) were dissolved in absolute ethanol (500 mL), and cooled to 0° C. before the addition of DCC (42.2 g; 0.204 mol). The ice bath was removed after 5 minutes and stirring was continued for 2 more hours. The precipitated DCU (32.5 g dried) was removed by filtration and washed with ether (3×100 mL). The combined filtrate was washed successively with diluted potassium hydrogen sulfate (2×400 mL), diluted sodium hydrogencarbonate (2×400 mL) and saturated sodium chloride (1×400 mL). The organic phase was filtered, dried ($MgSO_4$) and evaporated to dryness, in vacuo, which yielded 66.1 g of an oily substance which contained some DCU.

The oil was dissolved in absolute ethanol (600 mL) and 10% palladium on carbon (6.6 g) was added. The solution was hydrogenated at atmospheric pressure, where the reservoir was filled with 2 N sodium hydroxide. After 4 hours, 3.3 L was consumed out of the theoretical 4.2 L. The reaction mixture was filtered through celite and evaporated to dryness, in vacuo, affording 39.5 g (94%) of an oily substance. A 13 g portion of the oily substance was purified by silica gel (600 g $SiO_2$) chromatography. After elution with 20% petroleum ether in methylene chloride (300 mL), the title compound was eluted with 5% methanol in methylene chloride (1700 mL). The solvent was removed from the fractions with satisfactory purity, in vacuo and the yield was 8.49 g. Alternatively 10 g of the crude material was purified by KugelRohr distillation. $^1$H-NMR (250 MHZ, $CD_3OD$); 4.77 (b. s, NH); 4.18 (q, 2H, MeC$\underline{H}_2$—); 3.38 (s, 2H, NC$\underline{H}_2$CO$_2$Et); 3.16 (t, 2H, BocNHC$\underline{H}_2$CH$_2$); 2.68 (t, 2H, BocNHCH$_2$C$\underline{H}_2$); 1.43 (s, 9H, $^t$Bu) and 1.26 (t, 3H, CH$_3$) $^{13}$C-NMR 171.4 ($\underline{C}$OEt); 156.6 (CO); 78.3 ((CH$_3$)$_3\underline{C}$); 59.9 (CH$_2$); 49.0 (CH$_2$); 48.1 (CH$_2$); 39.0 (CH$_2$); 26.9 (CH$_2$) and 12.6 (CH$_3$).

EXAMPLE 11

Methyl α-formylsuccinate

In a modification of the procedure of Fissekis and Sweet, *Biochemistry* 1970, 9, 3136–42, sodium methoxide (40.5 g, 0.75 mol) was suspended in dry ether (500 mL) and stirred under nitrogen at 0° C. A mixture of dimethylsuccinate (65.4 mL, 0.50 mol) and methylformate (123 mL, 2.00 mol) was added dropwise over 30 minutes. The reaction mixture was stirred at 0° C. for 2 hours and then at room temperature overnight. Subsequently, the reaction mixture was evaporated to a viscous brown residue which was washed once with petroleum ether and then dissolved in 3 M hydrochloric acid (160 mL). This solution was made weakly acidic with concentrated hydrochloric acid and then extracted with dichloromethane (4×250 mL). The organic phase was dried (MgSO$_4$), filtered and evaporated under reduced pressure. The resulting residue was distilled in a kugelrohr apparatus at 60° C. and 0.6 mBar yielding 52.3 g of a mixture of the title compound and dimethyl succinate in the molar ratio 80:20 (determined by NMR) as a colorless oil. This mixture can be used directly in the following preparation. The product can be isolated free of dimethyl succinate by exchanging the extraction with dichloromethane with a continuous extraction with diethyl ether. However, in our hands this reduced the yield to 34%. Fissekis and Sweet,ibid, had reported a 62% yield. $^1$H-NMR (DMSO-d$_6$/TMS): δ=3.20 (s, 2H, CH$_2$); 3.59 (s, 3H, OMe); 3.61 (s, 3H, OMe); 7.73 (s, 1H, C_HOH); 10.86 (br s, 1H, CHO_H). $^{13}$C-NMR (DMSO-d$_6$/TMS): δ=28.9 (CH$_2$); 51.0 (OMe); 51.6 (OMe); 102.1 (C_=CHOH); 156.6 (CHOH); 168.3 (COO); 171.7 (COO).

EXAMPLE 12

Isocytosin-5-ylacetic acid

In a modification of the procedure of Beran et al., *Collect. Czech. Chem. Commun.* 1983, 48, 292–298, sodium methoxide (41.9 g, 0.78 mol) was dissolved in dry methanol (200 mL) and guanidine hydrochloride (49.4 g, 0.52 mol) was added. The mixture was stirred for 10 minutes under nitrogen at room temperature. A solution of methyl α-formylsuccinate (30.0 g, 0.17 mol) in dry methanol (100 mL) was added to the mixture. The reaction mixture was refluxed under nitrogen for 3 hours and then stirred at room temperature overnight. Subsequently, the reaction mixture was filtered, and the filter cake was washed once with methanol. The collected filtrate and washing were evaporated under reduced pressure. The resulting residue was dissolved in water (80 mL) and the solution was acidified with concentrated hydrochloric acid to pH 4.2. After having been stirred at 0° C. the mixture was filtered, the precipitate washed once with water and then freeze-dried leaving 28.29 g (97%) of the title compound as a white solid. Calcd. for C$_6$H$_7$N$_3$O$_3$ 1/2H$_2$O: C, 40.45; H, 4.53; N, 23.59. Found: C, 40.13; H, 4.22; N, 23.26.

Due to the poor solubility properties of the product it was further characterized as its sodium salt. Isocytosin-5-ylacetic acid (0.42 g, 2.5 mmol) and sodium bicarbonate were dissolved in boiling water (35 mL). The solution was cooled and evaporated. The residue was dissolved in water (6 mL) and ethanol (4 mL) and isopropanol (8 mL) was added. The sodium salt of isocytosin-5-ylacetic acid was collected by filtration, washed with absolute ethanol and petroleum ether and dried to yield 0.31 g (65%) as white crystals. $^1$H-NMR (D$_2$O/TMS): δ=3.10 (s, 2H, CH$_2$COO); 7.40 (s, 1H, H-6). $^{13}$C-NMR (DMSO-d$_6$/TMS): δ=34.8 (C_H$_2$COO); 112.0 (C-5); 145.6–146.5 (m, C-2); 155.1 (C-6); 169.4 (C-4); 179.3 (COOH). MS (FAB+) m/z (%): 192 (100, M+H).

EXAMPLE 13

Methyl isocytosin-5-ylacetate

Thionylchloride (3.6 mL, 50 mmol) was added to stirred methanol (210 mL) at −40° C. under nitrogen. Isocytosin-5-ylacetic acid (7.0 g, 41 mmol) was added and the reaction mixture was stirred at room temperature for 1 hour, at 60° C. for 3 hours and overnight at room temperature. The reaction mixture was evaporated to dryness and the residue was dissolved in saturated aqueous sodium bicarbonate (80 mL) giving a foamy precipitate. 4 M hydrochloric acid was added to pH 6.5 and the suspension was stirred for 1 hour. The precipitate was collected by filtration, washed with water, recrystallized from water and freeze-dried yielding 4.66 g (62%) of methyl isocytosin-5-ylacetate as white crystals. $^1$H-NMR (DMSO-d$_6$/TMS): δ=3.28 (s, 2H, CH$_2$COO); 3.64 (s, 3H, COOMe); 6.87 (br s, 2H, NH$_2$); 7.54 (s, 1H, H-6). $^{13}$C-NMR (DMSO-d$_6$/TMS): δ=32.0 (C_H$_2$COO); 51.5 (COOM_e); 108.4 (C-5); 153.3 (C-2); 156.4 (C-6); 164.0 (C-4); 171.8 (CH$_2$C_OO). MS(FAB+) m/z (%): 184 (100, M+H). Calcd. for C$_7$H$_9$N$_3$O$_3$ 3/2H$_2$O: C, 40.00; H, 5.75; N, 19.99. Found: C, 40.18; H, 5.46; N, 20.30.

EXAMPLE 14

Methyl N-2- (benzyloxycarbonyl) isocytosin-5-ylacetate

Methyl isocytosin-5-ylacetate (9.5 g, 52 mmol) was dissolved in dry DMF (95 mL) and the solution was stirred at 0° C. under nitrogen. N-Benzyloxycarbonyl-N'-methyl-imidazolium triflate (37.99 g, 104 mmol) was added slowly. The reaction mixture was stirred for 30 minutes at 0° C. and then overnight at room temperature. Dichloromethane (800 mL) was added and the resultant mixture was washed with half-saturated aqueous sodium bicarbonate (2×400 mL), half-saturated aqueous potassium hydrogen sulfate (2×400 mL) and with brine (1×400 mL). The organic phase was dried (MgSO$_4$), filtered and evaporated under reduced pressure. The residue was recrystallized from methanol affording 13.32 g (81%) of the title compound as white crystals. $^1$H-NMR (DMSO-d$_6$/TMS): δ=3.43 (s, 2H, CH$_2$COO); 3.67 (s, 3H, COOMe); 5.30 (s, 2H, PhC_H$_2$); 7.43–7.52 (m, 5H, PhC_H$_2$); 7.77 (s, 1H, H-6). $^{13}$C-NMR (DMSO-d$_6$/TMS): δ=31.9 (C_H$_2$COO); 51.6 (COOM_e); 67.0 (PhC_H$_2$); 128.1–128.5 (m, P_hCH$_2$); 135.7 (P_hCH$_2$); 150.7 (Z-CO); 170.8 (COO). MS (FAB+) m/z (%): 318 (3.5, M+H) Calcd. for C$_{15}$H$_{15}$N$_3$O$_5$: C, 56.78; H, 4.76; N, 13.24. Found: C, 56.68; H, 4.79; N, 13.28.

EXAMPLE 15

N-2(Benzyloxycarbonyl)isocytosin-5-ylacetic acid

Methyl N-2(benzyloxycarbonyl) isocytosin-5-ylacetate (5.2 g, 16 mmol) was suspended in THF (52 mL) and cooled to 0° C. 1 M lithium hydroxide (49 mL, 49 mmol) was added and the reaction mixture was stirred at 0° C. for 25 minutes. Additional 1 M lithium hydroxide (20 mL, 20 mmol) was added and the mixture was stirred at 0° C. for 90 minutes. The product was precipitated by acidifying to pH 2 with 1 M hydrochloric acid, collected by filtration, washed once with water and dried to yield 4.12 g (83%) of white crystals. $^1$H-NMR (DMSO-d$_6$/TMS) : δ=3.33 (s, 2H, CH$_2$COO); 5.29 (s, 2H, PhC_H$_2$); 7.43–7.52 (m, 5H, P_hCH$_2$); 7.74 (s, 1H, H-6); 11.82 (br s, 3H, exchangeable protons). MS (FAB+) m/z (%): 304 (12, M+H) Calcd. for C$_{14}$H$_{13}$N$_3$O$_5$: C, 55.45; H, 4.32; N, 13.86. Found: C, 55.55; H, 4.46; N, 13.84.

EXAMPLE 16

Ethyl N-(2-BOC-aminoethyl)-N-(N-2 (benzyloxycarbonyl)isocytosin-5-ylacetyl)glycinate N-2(Benzyloxycarbonyl)isocytosin-5-ylacetic acid (2.0 g, 6.6 mmol) was transferred to a flask equipped with a stirring bar and a septum through which a flow of nitrogen was applied. Dry DMF (20 mL) and N-methylmorpholine (2.2 mL, 19.8 mmol) were added. The mixture was cooled to 0° C. and N'-Boc-aminoethyl glycine ethyl ester (1.8 g, 7.3 mmol) and O-benzotriazol-1-yl-N,N,N'-,N'-tetramethyluronium hexafluorophosphate (HBTU, 3.0 g, 7.9 mmol) were added. The reaction mixture was stirred under nitrogen for 4 h followed by addition of dichloromethane (100 mL). The organic phase was washed with half-saturated aqueous sodium bicarbonate (2×75 mL), half-saturated aqueous potassium hydrogen sulfate (2×75 mL) and with brine (1×75 mL), dried ($MgSO_4$), filtered and evaporated under reduced pressure. The residue was dissolved in ethyl acetate (50 mL), stirred at 0° C. for 10 minutes and filtered through celite which was washed with ethyl acetate. The collected filtrate and washing were concentrated to a volume of 10 mL. Diethyl ether (100 mL) was added and the resultant solution was stirred overnight at room temperature. The product was collected by filtration, washed once with diethyl ether and dried to yield 2.6 g (74%) of the title compound as white crystals. Due to hindered rotation around the amide bond several of the NMR signals are comprised of a major (ma) and minor (mi) component. $^1$H-NMR (DMSO-$d_6$/TMS): δ=1.20–1.30 (m, 3H, $CH_2\underline{CH_3}$); 1.45 (s, 9H, BOC); 3.05–3.52 (m, 6H, $NCH_2$, $CH_2N$, $CH_2CON$); 4.08 and 4.40 (s, ma and s, mi, respectively, 2H, $CH_2COO$); 4.15 and 4.25 (q, ma, J=7 Hz and q, mi, respectively, 2H, $\underline{CH_2}CH_3$); 5.29 (s, 2H, $Ph\underline{CH_2}$); 7.40–7.52 (m, 5H, $\underline{Ph}CH_2$); 7.64 and 7.67 (s, mi and s, ma, respectively, 1H, H-6) $^{13}$C-NMR (DMSO-$d_6$/TMS): δ=14.1 ($CH_2\underline{CH_3}$); 28.2 (BOC); 30.2 and 30.5 (ma and mi, respectively, $\underline{CH}CON$); 37.9 and 38.3 (mi and ma, respectively, $NCH_2$); 47.7 and 48. 0 (ma and mi, respectively, $CH_2N$); 50.2 ($\underline{CH_2}COO$); 60.4 and 61.0 (ma and mi, respectively, $\underline{CH_2}CH_3$); 67.0 ($Ph\underline{CH_2}$); 127.9–128.5 (m, $\underline{Ph}CH_2$); 135.8 ($\underline{Ph}CH_2$); 155.7 (C-6), 169.4 (CON); 170.0 (COO). MS (FAB+) m/z (%): 532 (3.5, M+H); 432 (3.5, M-BOC+H) Calcd. for $C_{25}H_{33}N_5O_8$: C, 56.49; H, 6.26; N, 13.17. Found: C, 56.46; H, 6.14; N, 12.86.

EXAMPLE 17

N-(2-BOC-aminoethyl)-N-(N-2-(benzyloxycarbonyl)isocytosin-5-ylacetyl-glycine

Ethyl N-(2-BOC-aminoethyl)-N-(N-2-(benzyloxycarbonyl)isocytosin-5-ylacetylglycinate (1.6 g, 3.0 mmol) was dissolved in methanol (16 mL) by gentle heating. The solution was cooled to 0° C. and 2 M sodium hydroxide (23 mL) was added. The reaction mixture was stirred at room temperature for 75 minutes and then cooled to 0° C. The pH was adjusted to 1.7 and the product was collected by filtration, washed once with water and dried to give 1.24 g (82%) of the title compound as white crystals.

Due to hindered rotation around the amide bond several of the NMR signals are comprised of a major (ma) and minor (mi) component. $^1$H-NMR (DMSO-$d_6$/TMS): δ=1.45 (s, 9H, BOC); 3.05–3.52 (m, 6H, $NCH_2$, $CH_2N$, $CH_2CON$); 4.01 and 4.29 (s, ma and s, mi, respectively, $CH_2COO$); 5.29 (s, 2H, $Ph\underline{CH_2}$); 7.40–7.51 (m, 5H, $\underline{Ph}CH_2$); 7.63 and 7.68 (s, mi and s, ma, respectively, 1H, H-6). $^{13}$C-NMR (DMSO-$d_6$/TMS): δ=28.2 (BOC); 30.2 and 30.5 (ma and mi, respectively, $\underline{CH_2}CON$); 37.9 and 38.3 (mi and ma, respectively, $NCH_2$); 47.5 and 47.9 (ma and mi, respectively, $CH_2N$); 50.2 ($\underline{CH_2}COO$); 67.0 ($Ph\underline{CH_2}$); 128.0–128.5 (m, $\underline{Ph}CH_2$); 135.8 ($\underline{Ph}CH_2$); 150.5 (Z-CO); 155.7 (C-6); 169.9 and 170.3 (ma and mi, respectively, CON); 170.8 and 171.2 (ma and mi, respectively, COO) MS (FAB+) m/z (%): 504 (16, M+H); 448 (3.5, M-t-Bu+H); 404 (23, M-BOC+H).

EXAMPLE 18

Synthesis of egl linked PNA H-TCT-CTT-T-(egl)$_3$-TTT-CTC-T-Lys-$NH_2$ (SEQ ID NO:19) (egl=—NH—$CH_2$—$CH_2$—O—$CH_2$—$CH_2$—O—$CH_2$—C(=O)—)

The protected egl linked PNA was assembled on a Boc-Lys(ClZ) functionalized MBHA resin with a substitution of approximately 0.10 mmol/g. The synthesis was initiated on 200 mg (dry weight) of t-Boc-Lys(ClZ)-MBHA resin, preswollen overnight in dichloromethane. The following steps were repeated until the desired sequence was obtained: (1) removal of the N-terminal t-Boc protecting group by treatment with 95:5 TFA/m-Cresol (2×4 min, 1 mL); (2) wash with 1:1 DMF/dichloromethane (3×1 min, 1 mL); (3) wash with pyridine (2×1 min,1 mL); (4) HBTU (18.0 mg, 0.48 mmol) and monomer (0.5 mmol, t-Boc-CZOH (25.1 mg), t-Boc-T-OH (19.2 mg) or t-Boc-egl-OH (13.1 mg)) was taken up in 1:1 DMF/pyridine (in the case of t-Boc-egl-OH neat DMF was used) and added DECA (16 mL, 1 mmol) to a final volume of 0.5 mL and the mixture was allowed to preactivate for 1 minute before addition to the resin where the coupling was allowed to proceed for 20 minutes at room temperature; (5) a few beads were removed for qualitative Kaiser test (Ninhydrin); (6) Wash with pyridine (2×1 min, 1 mL); (7) acylation with Rappoport's reagent (100 mg, 0.28 mmol) in DMF (1 mL); (8) Wash with 8:2 DMF/pipiridine; (9) wash with pyridine (3×1 min, 1 mL); (10) Wash with 1:1 DMF/dichloromethane (3×1 min, 1 mL).

When the desired sequence was obtained the resin was washed with neat dichloromethane (3×1 min, 1.5 mL) and then dried in a desiccator under vacuum. All qualitative Kaiser-tests were yellow with no coloration of the beads.

The bis aminoethylglycine (aeg)-PNA was cleaved from the resin and the permanent protection groups were removed. A solution of 1:8:1 TFA/DMS/m-cresol (50 mL) and a solution of 9:1 TFA/TFMSA (50 mL) were cooled on an icebath and added per 10 mg of dry resin. The reaction was allowed to proceed for 1 hour at room temperature and the resin was drained and washed with neat TFA (1×1 min, 1 mL). A solution of 8:1:1 TFA/TFMSA/m-cresol (100 μL) (cooled on an icebath) was added per 10 mg of dry resin. The reaction was allowed to proceed for 2 hours and the resin was drained and washed with TFA (1×1 min, 1 mL). The two TFA solutions combined and the aeg-PNA was precipitated by addition of dry ether. The precipitate was washed four times with dry ether. Yield: 12.7 mg (Purity>90%, purified by RP-HPLC, μBondapak C18). MS(FAB+) m/z: :(found/calcd) 4249/4247.

EXAMPLE 19 egl linked aeg-PNA Having Pseudoisocytosine (J) H-TJT-JTT-T-(egl)$_3$-TTT-CTC-T-Lys-$NH_2$ (SEQ ID NO:20)

The protected aeg-PNA was assembled on a Boc-Lys (ClZ) modified MBHA resin with a substitution of approximately 0.10 mmol/g. The synthesis was initiated on 100 mg (dry weight) of t-Boc-Lys(ClZ)-MBHA resin, preswollen overnight in dichloromethane. The bis aeg-PNA was synthesized as per the procedures of Example 15. In step (4) the aeg-pseudoisocytosine monomer of Examples 11 thru 15 (25.1 mg, 0.5 mmol) was used for the incorporation of the aeg-J unit. The bis aeg-PNA was cleaved from the resin as per known procedures described in references above. Yield: 5.5 mg (purity>90%, purified by RP-HPLC, μBondapak C18). MS(FAB+) m/z: :(found/calcd) 4748/4747.

PROCEDURE 1
Antimicrobial Assays
Tier I
  A. Streptococcus pyogenes (Gram Positive Specie)
  S. pyogenes [American Type Culture Collection (ATCC) #14289] is used in this bacterial growth assay. To initiate the exponential phase of bacterial growth prior to the assay, a sample of bacteria is grown for 6 hours in Todd Hewitt Broth (Difco 0492-17-6) at 37° C. then re-inoculated into fresh media and grown overnight at 37° C. The bacterial cells are collected by centrifugation for 10 minutes at 3200 rpm, diluted and absorbance read at 595 nm. Bacteria diluted in 2×Todd-Hewitt Broth (75 µL) are added to the compound mixtures (75µL) for a total volume of 150 µL. The assays are performed in 96-well microplates with approximately $1 \times 10^4$ colony forming units (CFU) per well. The plates are incubated at 37° C. and growth monitored over a 24 hour period by measuring the optical density at 595 nm using a BioRad model 3550 UV microplate reader. The percentage of growth relative to a well containing no test compound or library is determined. Ampicillin and tetracycline antibiotic controls are concurrently tested in each screening assay.

Compounds are assayed in duplicate at a single dose. Compounds which show inhibitory activity are re-tested in duplicate at multiple doses to determine minimum inhibitory concentration (MIC).

B. E. coli imp- (Gram Negative Specie)
  The strain E. coli imp- obtained from Spencer Benson (Sampson, B. A., Misra, R. & Benson, S. A., Genetics, 1989, 122, 491–501, Identification and characterization of a new gene of Escherichia coli K-12 involved in outer membrane permeability) is used in this bacterial growth assay. To initiate the exponential phase of bacterial growth prior to the assay, a sample of bacteria is grown for 6 hours in Mueller Hinton II Broth (BBL 12322) at 37° C. then re-inoculated into fresh media and grown overnight at 37° C. The bacterial cells are collected by centrifugation for 10 minutes at 3200 rpm, diluted and absorbance read at 595 nm. Bacteria diluted in 2×Mueller Hinton II Broth (75 µL) are added to the compound mixtures (75 µL) for a total volume of 150 µL. The assays are performed in 96-well microplates with approximately $1 \times 10^4$ colony forming units (CFU) per well. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic controls are concurrently tested in each screening assay.

Compounds are assayed in duplicate at a single dose. Compounds which show inhibitory activity are re-tested in duplicate at multiple doses to determine minimum inhibitory concentration (MIC). Such compounds may be further tested with one or more gram positive bacteria such as but not limited to the Tier II et seq. organisms described in the following sections.

Tier II
  A. Gram Positive
  The following gram positive strains are used to test compounds which showed activity in at least one of the Tier I organisms: Staphylococcus aureus (ATCC #13709), Enterococcus hirae (ATCC #10541), Streptococcus pyogenes (ATCC #49399). To initiate the exponential phase of bacterial growth prior to the assay, a sample of bacteria is grown for 6 hours in Todd Hewitt Broth (Difco 0492-17-6) at 37° C. then re-inoculated into fresh media and grown overnight at 37° C. The bacterial cells are collected by centrifugation for 10 minutes at 3200 rpm, diluted and absorbance read at 595 nm. Bacteria diluted in 2×Todd Hewitt Broth (75 µL) are added to the compound mixtures (75 µL) for a total volume of 150 µL. The assays are performed in 96-well microplates with approximately $1 \times 10^4$ colony forming units (CFU) per well. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic controls are concurrently tested in each screening assay. Compounds are assayed in duplicate at multiple doses to determine minimum inhibitory concentration (MIC).

B. Gram Negative
  The following gram negative strains are used to test compounds which showed activity in at least one of the Tier I organisms: Escherichia coli (ATCC #25922), Klebsiella pneumoniae (ATCC #10031), Proteus vulgaris (ATCC #13315), and Pseudomonas aeruginosa (ATCC #9027). To initiate the exponential phase of bacterial growth prior to the assay, a sample of bacteria is grown for 6 hours in Mueller Hinton II Broth (BBL 12322) at 37° C. then re-inoculated into fresh media and grown overnight at 37° C. The bacterial cells are collected by centrifugation for 10 minutes at 3200 rpm, diluted and absorbance read at 595 nm. Bacteria diluted in 2×Mueller Hinton II Broth (75 µL) are added to the compound mixtures (75 µL) for a total volume of 150 µL. The assays are performed in 96-well microplates with approximately $1 \times 10^4$ colony forming units (CFU) per well. The plates are incubated at 37° C. and growth monitored over a 24 hour period by measuring the optical density at 595 nm using a BioRad model 3550 UV microplate reader. The percentage of growth relative to a well containing no compound is determined. Ampicillin, tetracycline and ciprofloxacin antibiotic controls are concurrently tested in each screening assay.

Compounds are assayed in duplicate at multiple doses to determine minimum inhibitory concentration (MIC).

Tier III
  A. Antifungal Assay (Candida albicans)
  The strain Candida albicans (ATCC #10231) is used. To initiate the exponential phase of yeast growth prior to the assay, a sample of yeast is grown overnight at 25° C. in YM Broth (Difco 0711-17-1). The yeast cells are collected by centrifugation for 10 minutes at 3200 rpm, diluted and absorbance read at 595 nm. Yeast diluted in 2×YM Broth (75 µL) are added to the compound mixtures (75 µL) for a total volume of 150 µL. The assays are performed in 96-well microplates with approximately $1 \times 10^4$ cells per well. The plates are incubated at 25° C. and growth monitored at 48 hours by visual inspection of yeast growth. Amphotericin B anti-fungal control is concurrently tested in each screening assay.

Compounds are assayed in duplicate at multiple doses to determine minimum inhibitory concentration (MIC).

B. Red Blood Cell Lysis Assay
  Compounds are tested for hemolysis of mammalian red blood cells. Horse red blood cells (Colorado Serum Co. #CS0004) are diluted 1:5 in 1×phosphate buffered saline (PBS). 50 µL diluted RBC's are added to 50 µL of test compound in 1×PBS (total volume=100 µL) in a round bottom 96-well microplate, mixed gently, and incubated 1 hour at 37° C. The microplate is then centrifuged for 5 minutes at 1000 rpm. The supernatant is diluted 1:5 (20 µL supernatant+80 µL 1×PBS) into a clean flat bottom 96-well microplate. Absorbance at 540 nm is read using a BioRad model 3550 UV microplate reader.

Compounds are tested in duplicate at multiple doses to determine the minimum hemolytic concentration (MHC).

Tier IV

RNA Binding Assay (In Vitro)

A. The effect of libraries on tat/TAR interactions

SPA method (scintillation proximity assay)

A fast assay targeting tat/TAR interactions was developed for high through-put screening. The assay is used to rapidly identify compounds which are capable of disrupting the interaction of HIV-1 tat protein with the TAR RNA stem/loop structure.

1. Materials

The C terminal basic binding domain of the tat protein (a 39 residue tat peptide, aa 48–86 of HIV-1 tat protein) was synthesized by a contract lab and further labeled with $^{125}I$ (specific activity 100 µCi/mL) at Amersham Life Sciences.

A 30 base RNA oligonucleotide (TAR oligonucleotide) consisting of the bulge and stem/loop structure of HIV TAR was synthesized at ISIS Pharmaceuticals and further labeled via conjugation with Biotin at the 3' end.

A PRB buffer was prepared consisting of: 50 mM Tris-HCl (pH 8.0), 0.01% NP-40, 10% glycerol, 1.5 MM $MgCl_2$ and 50 mM KCl.

Streptavidin coated SPA beads were purchased from Amersham Life Sciences.

Opaque 96 well plates were used purchased.

2. Methods

Streptavidin coated SPA beads are incubated for 20 minutes at room temperature in a PRB buffer with 0.1 µCi of the labeled peptide and 100 nM of the biotin conjugated RNA oligonucleotide. Incubations are performed in the presence or absence of test samples in a volume of 50 µl in an opaque 96 well plate. Following the incubation the plates are spun at 1000 rpm for 5 minutes to settle the SPA beads. The biotintylated TAR oligonucleotide binds the steptavidin coated SPA bead. The labeled tat peptide associated with the biotintylated TAR oligonucleotide excites the scintillant in the SPA bead, resulting in a quantifiable signal which can be read in the TopCount 96 well scintillation counter. Compounds that interfere with the tat/TAR interaction result in $^{125}I$ tat floating free in buffer where excited electrons are quenched before transferring energy to scintillant in the SPA bead. This is observed as a decrease in signal.

What is claimed is:

1. A method of killing or inhibiting growth of bacteria comprising contacting said bacteria with a peptide nucleic acid, wherein said peptide nucleic acid is complementary to a region of ribosomal RNA of said bacteria.

2. The method of claim 1 wherein said peptide nucleic acid is complementary in an antiparallel orientation to a region of ribosomal RNA of said bacteria.

3. A method of killing or inhibiting growth of bacteria comprising contacting said bacteria with a peptide nucleic acid and at least one antibiotic.

4. A method of killing or inhibiting growth of bacteria comprising contacting said bacteria with a peptide nucleic acid wherein a portion of said peptide nucleic acid is complementary with a region of ribosomal RNA of said bacteria and a further portion of said peptide nucleic acid is complementary with a region of messenger RNA of said bacteria.

5. The method of claim 4 further comprising contacting said bacteria with at least one antibiotic.

6. The method of claim 4 wherein said peptide nucleic acid is complementary in an antiparallel orientation to a region of ribosomal RNA of said bacteria and a further portion of said peptide nucleic acid is complementary in an antiparallel orientation to a region of messenger RNA in said bacteria.

7. An antibacterial pharmaceutical composition comprising peptide nucleic acid and a pharmaceutically acceptable carrier or diluent, wherein said peptide nucleic acid is targeted to a gene encoding a β-lactamase.

8. An antibacterial pharmaceutical composition comprising peptide nucleic acid and a pharmaceutically acceptable carrier or diluent, wherein said antibacterial pharmaceutical composition further comprises a -lactam antibacterial agent.

9. A method of treating a mammal suffering from a bacterial infection comprising administering one or more peptide nucleic acid compounds to the mammal, wherein said peptide nucleic acid is complementary to a region of ribosomal RNA of said bacteria.

10. The method of claim 9 wherein said peptide nucleic acid is complementary in an antiparallel orientation to a region of ribosomal RNA of said bacteria.

11. A method of treating a mammal suffering from a bacterial infection comprising administering one or more peptide nucleic acid compounds to the mammal, further comprising concurrent treatment with an antibiotic.

12. A method of disinfection comprising, selecting an object to be disinfected;

contacting said object with peptide nucleic acid; and rinsing said object with a sterile liquid to remove said peptide nucleic acid.

13. The method of claim 12 wherein said peptide nucleic acid is in the form of a solution and said object is contacted with said solution over substantially all solvent accessible areas of said object.

* * * * *

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
        (A) LENGTH: 14 bases
        (B) TYPE: nucleic acid
        (C) STRANDEDNESS: single
        (D) TOPOLOGY: linear (xi) SEQUENCE DESCRIPTION: SEQ ID NO: 1:

TGACCATGAT TACG          14

(2) INFORMATION FOR SEQ ID NO: 2:

(i) SEQUENCE CHARACTERISTICS:
        (A) LENGTH: 17 bases
        (B) TYPE: nucleic acid
        (C) STRANDEDNESS: single
        (D) TOPOLOGY: linear (xi) SEQUENCE DESCRIPTION: SEQ ID NO:2:

TACGTGTTTC CTGTGTG       17

(2) INFORMATION FOR SEQ ID NO: 3:

(i) SEQUENCE CHARACTERISTICS:
        (A) LENGTH: 17 bases
        (B) TYPE: nucleic acid
        (C) STRANDEDNESS: single
        (D) TOPOLOGY: linear (xi) SEQUENCE DESCRIPTION: SEQ ID NO: 3:

GAGTATTCAA CATTTCC       17

(2) INFORMATION FOR SEQ ID NO: 4:

(i) SEQUENCE CHARACTERISTICS:
            (A) LENGTH: 17 bases
            (B) TYPE: nucleic acid
            (C) STRANDEDNESS: single
            (D) TOPOLOGY: linear (xi) SEQUENCE DESCRIPTION: SEQ ID NO: 4:

ATTGTCTTCC TTTTTCA                                                                  17

(2) INFORMATION FOR SEQ ID NO: 5:

(i) SEQUENCE CHARACTERISTICS:
            (A) LENGTH: 15 bases
            (B) TYPE: nucleic acid
            (C) STRANDEDNESS: single
            (D) TOPOLOGY: linear (ix) FEATURE:
            (A) NAME/KEY: Modified-site
            (B) LOCATION: 1
            (D) OTHER INFORMATION:N-acetyl(2-aminoethyl)glycine backbone (ix) FEATURE:
            (A) NAME/KEY: Modified-site
            (B) LOCATION: 2
            (D) OTHER INFORMATION:N-acetyl(2-aminoethyl)glycine backbone (ix) FEATURE:
            (A) NAME/KEY: Modified-site
            (B) LOCATION: 3
            (D) OTHER INFORMATION:N-acetyl(2-aminoethyl)glycine backbone (ix) FEATURE:
            (A) NAME/KEY: Modified-site
            (B) LOCATION: 4
            (D) OTHER INFORMATION:N-acetyl(2-aminoethyl)glycine backbone (ix) FEATURE:
            (A) NAME/KEY: Modified-site
            (B) LOCATION: 5
            (D) OTHER INFORMATION:N-acetyl(2-aminoethyl)glycine backbone (ix) FEATURE:
            (A) NAME/KEY:Modified-site
            (B) LOCATION: 6
            (D) OTHER INFORMATION:N-acetyl(2-aminoethyl)glycine backbone (ix) FEATURE:
            (A) NAME/KEY: Modified-site
            (B) LOCATION: 7
            (D) OTHER INFORMATION:N-acetyl(2-aminoethyl)glycine backbone (ix) FEATURE:
            (A) NAME/KEY: Modified-site
            (B) LOCATION: 8
            (D) OTHER INFORMATION:N-acetyl(2-aminoethyl)glycine backbone (ix) FEATURE:
            (A) NAME/KEY: Modified-site
            (B) LOCATION: 9
            (D) OTHER INFORMATION:N-acetyl(2-aminoethyl)glycine backbone (ix) FEATURE:
            (A) NAME/KEY: Modified-site
            (B) LOCATION: 10
            (D) OTHER INFORMATION:N-acetyl(2-aminoethyl)glycine backbone (ix) FEATURE:
            (A) NAME/KEY: Modified-site
            (B) LOCATION: 11
            (D) OTHER INFORMATION:N-acetyl(2-aminoethyl)glycine backbone (ix) FEATURE:
            (A) NAME/KEY: Modified-site
            (B) LOCATION: 12
            (D) OTHER INFORMATION:N-acetyl(2-aminoethyl)glycine backbone

```
    (ix) FEATURE:
         (A) NAME/KEY: Modified-site
         (B) LOCATION: 13
         (D) OTHER INFORMATION:N-acetyl(2-aminoethyl)glycine backbone (ix) FEATURE:
         (A) NAME/KEY: Modified-site
         (B) LOCATION: 14
         (D) OTHER INFORMATION:N-acetyl(2-aminoethyl)glycine backbone (ix) FEATURE:
         (A) NAME/KEY: Modified-site
         (B) LOCATION: 15
         (D) OTHER INFORMATION:N-[acetyl(2-aminoethyl)]-C-lysine-
             glycine backbone (xi) SEQUENCE DESCRIPTION: SEQ ID NO: 5:

GGTCATAGCT GTTTC                                                    15

(2) INFORMATION FOR SEQ ID NO: 6:

(i) SEQUENCE CHARACTERISTICS:
        (A) LENGTH: 15 bases
        (B) TYPE: nucleic acid
        (C) STRANDEDNESS: single
        (D) TOPOLOGY: linear (ix) FEATURE:
         (A) NAME/KEY: Modified-site
         (B) LOCATION: 1
         (D) OTHER INFORMATION:N-acetyl(2-aminoethyl)glycine backbone (ix) FEATURE:
         (A) NAME/KEY: Modified-site
         (B) LOCATION: 2
         (D) OTHER INFORMATION:N-acetyl(2-aminoethyl)glycine backbone (ix) FEATURE:
         (A) NAME/KEY: Modified-site
         (B) LOCATION: 3
         (D) OTHER INFORMATION:N-acetyl(2-aminoethyl)glycine backbone (ix) FEATURE:
         (A) NAME/KEY: Modified-site
         (B) LOCATION: 4
         (D) OTHER INFORMATION:N-acetyl(2-aminoethyl)glycine backbone (ix) FEATURE:
         (A) NAME/KEY: Modified-site
         (B) LOCATION: 5
         (D) OTHER INFORMATION:N-acetyl(2-aminoethyl)glycine backbone (ix) FEATURE:
         (A) NAME/KEY: Modified-site
         (B) LOCATION: 6
         (D) OTHER INFORMATION:N-acetyl(2-aminoethyl)glycine backbone (ix) FEATURE:
         (A) NAME/KEY: Modified-site
         (B) LOCATION: 7
         (D) OTHER INFORMATION:N-acetyl(2-aminoethyl)glycine backbone (ix) FEATURE:
         (A) NAME/KEY: Modified-site
         (B) LOCATION: 8
         (D) OTHER INFORMATION:N-acetyl(2-aminoethyl)glycine backbone (ix) FEATURE:
         (A) NAME/KEY: Modified-site
         (B) LOCATION: 9
         (D) OTHER INFORMATION:N-acetyl(2-aminoethyl)glycine backbone (ix) FEATURE:
         (A) NAME/KEY: Modified-site
         (B) LOCATION: 10
         (D) OTHER INFORMATION:N-acetyl(2-aminoethyl)glycine backbone
```

```
    (ix) FEATURE:
          (A) NAME/KEY: Modified-site
          (B) LOCATION: 11
          (D) OTHER INFORMATION:N-acetyl(2-aminoethyl)glycine backbone (ix) FEATURE:
          (A) NAME/KEY: Modified-site
          (B) LOCATION: 12
          (D) OTHER INFORMATION:N-acetyl(2-aminoethyl)glycine backbone (ix) FEATURE:
          (A) NAME/KEY: Modified-site
          (B) LOCATION: 13
          (D) OTHER INFORMATION:N-acetyl(2-aminoethyl)glycine backbone (ix) FEATURE:
          (A) NAME/KEY: Modified-site
          (B) LOCATION: 14
          (D) OTHER INFORMATION:N-acetyl(2-aminoethyl)glycine backbone (ix) FEATURE:
          (A) NAME/KEY: Modified-site
          (B) LOCATION: 15
          (D) OTHER INFORMATION:N-[acetyl(2-aminoethyl)]-C-lysine-
              glycine backbone (xi) SEQUENCE DESCRIPTION: SEQ ID NO: 6:

TACTCATACT CTTCC                                                  15

(2) INFORMATION FOR SEQ ID NO: 7:

(i) SEQUENCE CHARACTERISTICS:
          (A) LENGTH: 15 bases
          (B) TYPE: nucleic acid
          (C) STRANDEDNESS: single
          (D) TOPOLOGY: linear (ix) FEATURE:
          (A) NAME/KEY: Modified-site
          (B) LOCATION: 1
          (D) OTHER INFORMATION:N-acetyl(2-aminoethyl)glycine backbone (ix) FEATURE:
          (A) NAME/KEY: Modified-site
          (B) LOCATION: 2
          (D) OTHER INFORMATION:N-acetyl(2-aminoethyl)glycine backbone (ix) FEATURE:
          (A) NAME/KEY: Modified-site
          (B) LOCATION: 3
          (D) OTHER INFORMATION:N-acetyl(2-aminoethyl)glycine backbone (ix) FEATURE:
          (A) NAME/KEY: Modified-site
          (B) LOCATION: 4
          (D) OTHER INFORMATION:N-acetyl(2-aminoethyl)glycine backbone (ix) FEATURE:
          (A) NAME/KEY: Modified-site
          (B) LOCATION: 5
          (D) OTHER INFORMATION:N-acetyl(2-aminoethyl)glycine backbone (ix) FEATURE:
          (A) NAME/KEY: Modified-site
          (B) LOCATION: 6
          (D) OTHER INFORMATION:N-acetyl(2-aminoethyl)glycine backbone (ix) FEATURE:
          (A) NAME/KEY: Modified-site
          (B) LOCATION: 7
          (D) OTHER INFORMATION:N-acetyl(2-aminoethyl)glycine backbone (ix) FEATURE:
          (A) NAME/KEY: Modified-site
          (B) LOCATION: 8
          (D) OTHER INFORMATION:N-acetyl(2-aminoethyl)glycine backbone
```

```
    (ix) FEATURE:
          (A) NAME/KEY: Modified-site
          (B) LOCATION: 9
          (D) OTHER INFORMATION:N-acetyl(2-aminoethyl)glycine backbone (ix) FEATURE:
          (A) NAME/KEY: Modified-site
          (B) LOCATION: 10
          (D) OTHER INFORMATION:N-acetyl(2-aminoethyl)glycine backbone (ix) FEATURE:
          (A) NAME/KEY: Modified-site
          (B) LOCATION: 11
          (D) OTHER INFORMATION:N-acetyl(2-aminoethyl)glycine backbone (ix) FEATURE:
          (A) NAME/KEY: Modified-site
          (B) LOCATION: 12
          (D) OTHER INFORMATION:N-acetyl(2-aminoethyl)glycine backbone (ix) FEATURE:
          (A) NAME/KEY: Modified-site
          (B) LOCATION: 13
          (D) OTHER INFORMATION:N-acetyl(2-aminoethyl)glycine backbone (ix) FEATURE:
          (A) NAME/KEY: Modified-site
          (B) LOCATION: 14
          (D) OTHER INFORMATION:N-acetyl(2-aminoethyl)glycine backbone (ix) FEATURE:
          (A) NAME/KEY: Modified-site
          (B) LOCATION: 15
          (D) OTHER INFORMATION:N-[acetyl(2-aminoethyl)]-C-lysine-
              glycine backbone (xi) SEQUENCE DESCRIPTION: SEQ ID NO: 7:

GAATACTCAT ACTCT                                                    15

(2) INFORMATION FOR SEQ ID NO: 8:

(i) SEQUENCE CHARACTERISTICS:
          (A) LENGTH: 15 bases
          (B) TYPE: nucleic acid
          (C) STRANDEDNESS: single
          (D) TOPOLOGY: linear (ix) FEATURE:
          (A) NAME/KEY: Modified-site
          (B) LOCATION: 1
          (D) OTHER INFORMATION:N-acetyl(2-aminoethyl)glycine backbone (ix) FEATURE:
          (A) NAME/KEY: Modified-site
          (B) LOCATION: 2
          (D) OTHER INFORMATION:N-acetyl(2-aminoethyl)glycine backbone (ix) FEATURE:
          (A) NAME/KEY: Modified-site
          (B) LOCATION: 3
          (D) OTHER INFORMATION:N-acetyl(2-aminoethyl)glycine backbone (ix) FEATURE:
          (A) NAME/KEY: Modified-site
          (B) LOCATION: 4
          (D) OTHER INFORMATION:N-acetyl(2-aminoethyl)glycine backbone (ix) FEATURE:
          (A) NAME/KEY: Modified-site
          (B) LOCATION: 5
          (D) OTHER INFORMATION:N-acetyl(2-aminoethyl)glycine backbone (ix) FEATURE:
          (A) NAME/KEY: Modified-site
          (B) LOCATION: 6
          (D) OTHER INFORMATION:N-acetyl(2-aminoethyl)glycine backbone
```

```
    (ix) FEATURE:
         (A) NAME/KEY: Modified-site
         (B) LOCATION: 7
         (D) OTHER INFORMATION:N-acetyl(2-aminoethyl)glycine backbone (ix) FEATURE:
         (A) NAME/KEY: Modified-site
         (B) LOCATION: 8
         (D) OTHER INFORMATION:N-acetyl(2-aminoethyl)glycine backbone (ix) FEATURE:
         (A) NAME/KEY: Modified-site
         (B) LOCATION: 9
         (D) OTHER INFORMATION:N-acetyl(2-aminoethyl)glycine backbone (ix) FEATURE:
         (A) NAME/KEY: Modified-site
         (B) LOCATION: 10
         (D) OTHER INFORMATION:N-acetyl(2-aminoethyl)glycine backbone (ix) FEATURE:
         (A) NAME/KEY: Modified-site
         (B) LOCATION: 11
         (D) OTHER INFORMATION:N-acetyl(2-aminoethyl)glycine backbone (ix) FEATURE:
         (A) NAME/KEY: Modified-site
         (B) LOCATION: 12
         (D) OTHER INFORMATION:N-acetyl(2-aminoethyl)glycine backbone (ix) FEATURE:
         (A) NAME/KEY: Modified-site
         (B) LOCATION: 13
         (D) OTHER INFORMATION:N-acetyl(2-aminoethyl)glycine backbone (ix) FEATURE:
         (A) NAME/KEY: Modified-site
         (B) LOCATION: 14
         (D) OTHER INFORMATION:N-acetyl(2-aminoethyl)glycine backbone (ix) FEATURE:
         (A) NAME/KEY: Modified-site
         (B) LOCATION: 15
         (D) OTHER INFORMATION:N-[acetyl(2-aminoethyl)]-C-lysine-
             glycine backbone (xi) SEQUENCE DESCRIPTION: SEQ ID NO: 8:

ACGCCACATC TTCGC                                                      15

(2) INFORMATION FOR SEQ ID NO: 9:

(i) SEQUENCE CHARACTERISTICS:
        (A) LENGTH: 15 bases
        (B) TYPE: nucleic acid
        (C) STRANDEDNESS: single
        (D) TOPOLOGY: linear (ix) FEATURE:
         (A) NAME/KEY: Modified-site
         (B) LOCATION: 1
         (D) OTHER INFORMATION:N-acetyl(2-aminoethyl)glycine backbone (ix) FEATURE:
         (A) NAME/KEY: Modified-site
         (B) LOCATION: 2
         (D) OTHER INFORMATION:N-pseudo isocytosine-acetyl(2-
             aminoethyl)glycine backbone (ix) FEATURE:
         (A) NAME/KEY: Modified-site
         (B) LOCATION: 3
         (D) OTHER INFORMATION:N-pseudo isocytosine-acetyl(2-
             aminoethyl)glycine backbone (ix) FEATURE:
         (A) NAME/KEY: Modified-site
         (B) LOCATION: 4
```

```
            (D) OTHER INFORMATION:N-pseudo isocytosine-acetyl(2-
                aminoethyl)glycine backbone (ix) FEATURE:
            (A) NAME/KEY: Modified-site
            (B) LOCATION: 5
            (D) OTHER INFORMATION:N-acetyl(2-aminoethyl)glycine backbone (ix) FEATURE:
            (A) NAME/KEY: Modified-site
            (B) LOCATION: 6
            (D) OTHER INFORMATION:N-acetyl(2-aminoethyl)glycine backbone (ix) FEATURE:
            (A) NAME/KEY: Modified-site
            (B) LOCATION: 7
            (D) OTHER INFORMATION:N-pseudo isocytosine-acetyl(2-
                aminoethyl)glycine backbone (ix) FEATURE:
            (A) NAME/KEY: Modified-site
            (B) LOCATION: 8
            (D) OTHER INFORMATION:(O-2-aminoethyl-O'-acetyl-
                ethyleneglycol)3

(ix) FEATURE:
            (A) NAME/KEY: Modified-site
            (B) LOCATION: 9
            (D) OTHER INFORMATION:N-acetyl(2-aminoethyl)glycine backbone (ix) FEATURE:
            (A) NAME/KEY: Modified-site
            (B) LOCATION: 10
            (D) OTHER INFORMATION:N-acetyl(2-aminoethyl)glycine backbone (ix) FEATURE:
            (A) NAME/KEY: Modified-site
            (B) LOCATION: 11
            (D) OTHER INFORMATION:N-acetyl(2-aminoethyl)glycine backbone (ix) FEATURE:
            (A) NAME/KEY: Modified-site
            (B) LOCATION: 12
            (D) OTHER INFORMATION:N-acetyl(2-aminoethyl)glycine backbone (ix) FEATURE:
            (A) NAME/KEY: Modified-site
            (B) LOCATION: 13
            (D) OTHER INFORMATION:N-acetyl(2-aminoethyl)glycine backbone (ix) FEATURE:
            (A) NAME/KEY: Modified-site
            (B) LOCATION: 14
            (D) OTHER INFORMATION:N-acetyl(2-aminoethyl)glycine backbone (ix) FEATURE:
            (A) NAME/KEY: Modified-site
            (B) LOCATION: 15
            (D) OTHER INFORMATION:N-[acetyl(2-aminoethyl)]-C-lysine-
                glycine backbone (xi) SEQUENCE DESCRIPTION: SEQ ID NO: 9:

TNNNTTNNCT TCCCT                                                     15

(2) INFORMATION FOR SEQ ID NO: 10:

(i) SEQUENCE CHARACTERISTICS:
            (A) LENGTH: 15 bases
            (B) TYPE: nucleic acid
            (C) STRANDEDNESS: single
            (D) TOPOLOGY: linear (ix) FEATURE:
            (A) NAME/KEY: Modified-site
            (B) LOCATION: 1
            (D) OTHER INFORMATION:N-pseudo isocytosine-acetyl(2-
                aminoethyl)glycine backbone
```

```
(ix) FEATURE:
    (A) NAME/KEY: Modified-site
    (B) LOCATION: 2
    (D) OTHER INFORMATION:N-acetyl(2-aminoethyl)glycine backbone (ix) FEATURE:
    (A) NAME/KEY: Modified-site
    (B) LOCATION: 3
    (D) OTHER INFORMATION:N-acetyl(2-aminoethyl)glycine backbone (ix) FEATURE:
    (A) NAME/KEY: Modified-site
    (B) LOCATION: 4
    (D) OTHER INFORMATION:N-acetyl(2-aminoethyl)glycine backbone (ix) FEATURE:
    (A) NAME/KEY: Modified-site
    (B) LOCATION: 5
    (D) OTHER INFORMATION:N-pseudo isocytosine-acetyl(2-
        aminoethyl)glycine backbone (ix) FEATURE:
    (A) NAME/KEY: Modified-site
    (B) LOCATION: 6
    (D) OTHER INFORMATION:N-pseudo isocytosine-acetyl(2-
        aminoethyl)glycine backbone (ix) FEATURE:
    (A) NAME/KEY: Modified-site
    (B) LOCATION: 7
    (D) OTHER INFORMATION:N-acetyl(2-aminoethyl)glycine backbone (ix) FEATURE:
    (A) NAME/KEY: Modified-site
    (B) LOCATION: 8
    (D) OTHER INFORMATION:(O-2-aminoethyl-O'-acetyl-
        ethyleneglycol)3

(ix) FEATURE:
    (A) NAME/KEY: Modified-site
    (B) LOCATION: 9
    (D) OTHER INFORMATION:N-acetyl(2-aminoethyl)glycine backbone (ix) FEATURE:
    (A) NAME/KEY: Modified-site
    (B) LOCATION: 10
    (D) OTHER INFORMATION:N-acetyl(2-aminoethyl)glycine backbone (ix) FEATURE:
    (A) NAME/KEY: Modified-site
    (B) LOCATION: 11
    (D) OTHER INFORMATION:N-acetyl(2-aminoethyl)glycine backbone (ix) FEATURE:
    (A) NAME/KEY: Modified-site
    (B) LOCATION: 12
    (D) OTHER INFORMATION:N-acetyl(2-aminoethyl)glycine backbone (ix) FEATURE:
    (A) NAME/KEY: Modified-site
    (B) LOCATION: 13
    (D) OTHER INFORMATION:N-acetyl(2-aminoethyl)glycine backbone (ix) FEATURE:
    (A) NAME/KEY: Modified-site
    (B) LOCATION: 14
    (D) OTHER INFORMATION:N-acetyl(2-aminoethyl)glycine backbone (ix) FEATURE:
    (A) NAME/KEY: Modified-site
    (B) LOCATION: 15
    (D) OTHER INFORMATION:N-[acetyl(2-aminoethyl)]-C-lysine-
        glycine backbone (xi) SEQUENCE DESCRIPTION: SEQ ID NO: 10:

NTTTNNTNTC CTTTC                                              15
```

(2) INFORMATION FOR SEQ ID NO: 11:

(i) SEQUENCE CHARACTERISTICS:
        (A) LENGTH: 15 bases
        (B) TYPE: nucleic acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION:N-acetyl(2-aminoethyl)glycine backbone (ix) FEATURE:
        (A) NAME/KEY: Modified-site
        (B) LOCATION: 2
        (D) OTHER INFORMATION:N-acetyl(2-aminoethyl)glycine backbone (ix) FEATURE:
        (A) NAME/KEY: Modified-site
        (B) LOCATION: 3
        (D) OTHER INFORMATION:N-acetyl(2-aminoethyl)glycine backbone (ix) FEATURE:
        (A) NAME/KEY: Modified-site
        (B) LOCATION: 4
        (D) OTHER INFORMATION:N-acetyl(2-aminoethyl)glycine backbone (ix) FEATURE:
        (A) NAME/KEY: Modified-site
        (B) LOCATION: 5
        (D) OTHER INFORMATION:N-acetyl(2-aminoethyl)glycine backbone (ix) FEATURE:
        (A) NAME/KEY: Modified-site
        (B) LOCATION: 6
        (D) OTHER INFORMATION:N-acetyl(2-aminoethyl)glycine backbone (ix) FEATURE:
        (A) NAME/KEY: Modified-site
        (B) LOCATION: 7
        (D) OTHER INFORMATION:N-acetyl(2-aminoethyl)glycine backbone (ix) FEATURE:
        (A) NAME/KEY: Modified-site
        (B) LOCATION: 8
        (D) OTHER INFORMATION:N-acetyl(2-aminoethyl)glycine backbone (ix) FEATURE:
        (A) NAME/KEY: Modified-site
        (B) LOCATION: 9
        (D) OTHER INFORMATION:N-acetyl(2-aminoethyl)glycine backbone (ix) FEATURE:
        (A) NAME/KEY: Modified-site
        (B) LOCATION: 10
        (D) OTHER INFORMATION:N-acetyl(2-aminoethyl)glycine backbone (ix) FEATURE:
        (A) NAME/KEY: Modified-site
        (B) LOCATION: 11
        (D) OTHER INFORMATION:N-acetyl(2-aminoethyl)glycine backbone (ix) FEATURE:
        (A) NAME/KEY: Modified-site
        (B) LOCATION: 12
        (D) OTHER INFORMATION:N-acetyl(2-aminoethyl)glycine backbone (ix) FEATURE:
        (A) NAME/KEY: Modified-site
        (B) LOCATION: 13
        (D) OTHER INFORMATION:N-acetyl(2-aminoethyl)glycine backbone (ix) FEATURE:
        (A) NAME/KEY: Modified-site
        (B) LOCATION: 14
        (D) OTHER INFORMATION:N-acetyl(2-aminoethyl)glycine backbone

```
    (ix) FEATURE:
          (A) NAME/KEY: Modified-site
          (B) LOCATION: 15
          (D) OTHER INFORMATION:N-[acetyl(2-aminoethyl)]-C-lysine-
              glycine backbone (xi) SEQUENCE DESCRIPTION: SEQ ID NO: 11:

CATACTCTTT CTCCT                                                          15

(2) INFORMATION FOR SEQ ID NO: 12:

(i) SEQUENCE CHARACTERISTICS:
          (A) LENGTH: 25 bases
          (B) TYPE: nucleic acid
          (C) STRANDEDNESS: single
          (D) TOPOLOGY: linear (ix) FEATURE:
          (A) NAME/KEY: Modified-site
          (B) LOCATION: 1
          (D) OTHER INFORMATION:N-acetyl(2-aminoethyl)glycine backbone (ix) FEATURE:
          (A) NAME/KEY: Modified-site
          (B) LOCATION: 2
          (D) OTHER INFORMATION:N-acetyl(2-aminoethyl)glycine backbone (ix) FEATURE:
          (A) NAME/KEY: Modified-site
          (B) LOCATION: 3
          (D) OTHER INFORMATION:N-pseudo isocytosine-acetyl(2-
              aminoethyl)glycine backbone (ix) FEATURE:
          (A) NAME/KEY: Modified-site
          (B) LOCATION: 4
          (D) OTHER INFORMATION:N-acetyl(2-aminoethyl)glycine backbone (ix) FEATURE:
          (A) NAME/KEY: Modified-site
          (B) LOCATION: 5
          (D) OTHER INFORMATION:N-pseudo isocytosine-acetyl(2-
              aminoethyl)glycine backbone (ix) FEATURE:
          (A) NAME/KEY: Modified-site
          (B) LOCATION: 6
          (D) OTHER INFORMATION:N-pseudo isocytosine-acetyl(2-
              aminoethyl)glycine backbone (ix) FEATURE:
          (A) NAME/KEY: Modified-site
          (B) LOCATION: 7
          (D) OTHER INFORMATION:N-pseudo isocytosine-acetyl(2-
              aminoethyl)glycine backbone (ix) FEATURE:
          (A) NAME/KEY: Modified-site
          (B) LOCATION: 8
          (D) OTHER INFORMATION:N-acetyl(2-aminoethyl)glycine backbone (ix) FEATURE:
          (A) NAME/KEY: Modified-site
          (B) LOCATION: 9
          (D) OTHER INFORMATION:N-acetyl(2-aminoethyl)glycine backbone (ix) FEATURE:
          (A) NAME/KEY: Modified-site
          (B) LOCATION: 10
          (D) OTHER INFORMATION:N-acetyl(2-aminoethyl)glycine backbone (ix) FEATURE:
          (A) NAME/KEY: Modified-site
          (B) LOCATION: 11
          (D) OTHER INFORMATION:N-pseudo isocytosine-acetyl(2-
              aminoethyl)glycine backbone
```

```
    (ix) FEATURE:
         (A) NAME/KEY: Modified-site
         (B) LOCATION: 12
         (D) OTHER INFORMATION:(O-2-aminoethyl-O'-acetyl-
             ethyleneglycol)3

(ix) FEATURE:
         (A) NAME/KEY: Modified-site
         (B) LOCATION: 13
         (D) OTHER INFORMATION:N-acetyl(2-aminoethyl)glycine backbone (ix) FEATURE:
         (A) NAME/KEY: Modified-site
         (B) LOCATION: 14
         (D) OTHER INFORMATION:N-acetyl(2-aminoethyl)glycine backbone (ix) FEATURE:
         (A) NAME/KEY: Modified-site
         (B) LOCATION: 15
         (D) OTHER INFORMATION:N-acetyl(2-aminoethyl)glycine backbone (ix) FEATURE:
         (A) NAME/KEY: Modified-site
         (B) LOCATION: 16
         (D) OTHER INFORMATION:N-acetyl(2-aminoethyl)glycine backbone (ix) FEATURE:
         (A) NAME/KEY: Modified-site
         (B) LOCATION: 17
         (D) OTHER INFORMATION:N-acetyl(2-aminoethyl)glycine backbone (ix) FEATURE:
         (A) NAME/KEY: Modified-site
         (B) LOCATION: 18
         (D) OTHER INFORMATION:N-acetyl(2-aminoethyl)glycine backbone (ix) FEATURE:
         (A) NAME/KEY: Modified-site
         (B) LOCATION: 19
         (D) OTHER INFORMATION:N-acetyl(2-aminoethyl)glycine backbone (ix) FEATURE:
         (A) NAME/KEY: Modified-site
         (B) LOCATION: 20
         (D) OTHER INFORMATION:N-acetyl(2-aminoethyl)glycine backbone (ix) FEATURE:
         (A) NAME/KEY: Modified-site
         (B) LOCATION: 21
         (D) OTHER INFORMATION:N-acetyl(2-aminoethyl)glycine backbone (ix) FEATURE:
         (A) NAME/KEY: Modified-site
         (B) LOCATION: 22
         (D) OTHER INFORMATION:N-acetyl(2-aminoethyl)glycine backbone (ix) FEATURE:
         (A) NAME/KEY: Modified-site
         (B) LOCATION: 23
         (D) OTHER INFORMATION:N-acetyl(2-aminoethyl)glycine backbone (ix) FEATURE:
         (A) NAME/KEY: Modified-site
         (B) LOCATION: 24
         (D) OTHER INFORMATION:N-acetyl(2-aminoethyl)glycine backbone (ix) FEATURE:
         (A) NAME/KEY: Modified-site
         (B) LOCATION: 25
         (D) OTHER INFORMATION:N-[acetyl(2-aminoethyl)]-C-lysine-
             glycine backbone (xi) SEQUENCE DESCRIPTION: SEQ ID NO: 12:

TTNTNNNTTT NTNTCTTTCC GTCTT                                              25

(2) INFORMATION FOR SEQ ID NO: 13:
```

```
    (i) SEQUENCE CHARACTERISTICS:
        (A) LENGTH: 15 bases
        (B) TYPE: nucleic acid
        (C) STRANDEDNESS: single
        (D) TOPOLOGY: linear (ix) FEATURE:
     (A) NAME/KEY: Modified-site
     (B) LOCATION: 1
     (D) OTHER INFORMATION:N-pseudo isocytosine-acetyl(2-
         aminoethyl)glycine backbone (ix) FEATURE:
     (A) NAME/KEY: Modified-site
     (B) LOCATION: 2
     (D) OTHER INFORMATION:N-acetyl(2-aminoethyl)glycine backbone (ix) FEATURE:
     (A) NAME/KEY: Modified-site
     (B) LOCATION: 3
     (D) OTHER INFORMATION:N-pseudo isocytosine-acetyl(2-
         aminoethyl)glycine backbone (ix) FEATURE:
     (A) NAME/KEY: Modified-site
     (B) LOCATION: 4
     (D) OTHER INFORMATION:N-acetyl(2-aminoethyl)glycine backbone (ix) FEATURE:
     (A) NAME/KEY: Modified-site
     (B) LOCATION: 5
     (D) OTHER INFORMATION:N-pseudo isocytosine-acetyl(2-
         aminoethyl)glycine backbone (ix) FEATURE:
     (A) NAME/KEY: Modified-site
     (B) LOCATION: 6
     (D) OTHER INFORMATION:N-pseudo isocytosine-acetyl(2-
         aminoethyl)glycine backbone (ix) FEATURE:
     (A) NAME/KEY: Modified-site
     (B) LOCATION: 7
     (D) OTHER INFORMATION:N-acetyl(2-aminoethyl)glycine backbone (ix) FEATURE:
     (A) NAME/KEY: Modified-site
     (B) LOCATION: 8
     (D) OTHER INFORMATION:(O-2-aminoethyl-O'-acetyl-ethylene
         glycol)3

(ix) FEATURE:
     (A) NAME/KEY: Modified-site
     (B) LOCATION: 9
     (D) OTHER INFORMATION:N-acetyl(2-aminoethyl)glycine backbone (ix) FEATURE:
     (A) NAME/KEY: Modified-site
     (B) LOCATION: 10
     (D) OTHER INFORMATION:N-acetyl(2-aminoethyl)glycine backbone (ix) FEATURE:
     (A) NAME/KEY: Modified-site
     (B) LOCATION: 11
     (D) OTHER INFORMATION:N-acetyl(2-aminoethyl)glycine backbone (ix) FEATURE:
     (A) NAME/KEY: Modified-site
     (B) LOCATION: 12
     (D) OTHER INFORMATION:N-acetyl(2-aminoethyl)glycine backbone (ix) FEATURE:
     (A) NAME/KEY: Modified-site
     (B) LOCATION: 13
     (D) OTHER INFORMATION:N-acetyl(2-aminoethyl)glycine backbone (ix) FEATURE:
     (A) NAME/KEY: Modified-site
     (B) LOCATION: 14
```

(D) OTHER INFORMATION:N-acetyl(2-aminoethyl)glycine backbone (ix) FEATURE:
    (A) NAME/KEY: Modified-site
    (B) LOCATION: 15
    (D) OTHER INFORMATION:N-[acetyl(2-aminoethyl)]-C-lysine-
        glycine backbone (xi) SEQUENCE DESCRIPTION: SEQ ID NO: 13:

```
NTNTNNTNTC CTCTC                                                15
```

(2) INFORMATION FOR SEQ ID NO: 14:

(i) SEQUENCE CHARACTERISTICS:
    (A) LENGTH: 12 bases
    (B) TYPE: nucleic acid
    (C) STRANDEDNESS: single
    (D) TOPOLOGY: linear (ix) FEATURE:
    (A) NAME/KEY: Modified-site
    (B) LOCATION: 1
    (D) OTHER INFORMATION:N-acetyl(2-aminoethyl)glycine backbone (ix) FEATURE:
    (A) NAME/KEY: Modified-site
    (B) LOCATION: 2
    (D) OTHER INFORMATION:N-acetyl(2-aminoethyl)glycine backbone (ix) FEATURE:
    (A) NAME/KEY: Modified-site
    (B) LOCATION: 3
    (D) OTHER INFORMATION:N-acetyl(2-aminoethyl)glycine backbone (ix) FEATURE:
    (A) NAME/KEY: Modified-site
    (B) LOCATION: 4
    (D) OTHER INFORMATION:N-acetyl(2-aminoethyl)glycine backbone (ix) FEATURE:
    (A) NAME/KEY: Modified-site
    (B) LOCATION: 5
    (D) OTHER INFORMATION:N-acetyl(2-aminoethyl)glycine backbone (ix) FEATURE:
    (A) NAME/KEY: Modified-site
    (B) LOCATION: 6
    (D) OTHER INFORMATION:N-acetyl(2-aminoethyl)glycine backbone (ix) FEATURE:
    (A) NAME/KEY: Modified-site
    (B) LOCATION: 7
    (D) OTHER INFORMATION:N-acetyl(2-aminoethyl)glycine backbone (ix) FEATURE:
    (A) NAME/KEY: Modified-site
    (B) LOCATION: 8
    (D) OTHER INFORMATION:N-acetyl(2-aminoethyl)glycine backbone (ix) FEATURE:
    (A) NAME/KEY: Modified-site
    (B) LOCATION: 9
    (D) OTHER INFORMATION:N-acetyl(2-aminoethyl)glycine backbone (ix) FEATURE:
    (A) NAME/KEY: Modified-site
    (B) LOCATION: 10
    (D) OTHER INFORMATION:N-acetyl(2-aminoethyl)glycine backbone (ix) FEATURE:
    (A) NAME/KEY: Modified-site
    (B) LOCATION: 11
    (D) OTHER INFORMATION:N-acetyl(2-aminoethyl)glycine backbone (ix) FEATURE:
    (A) NAME/KEY: Modified-site
    (B) LOCATION: 12

(D) OTHER INFORMATION:N-[acetyl(2-aminoethyl)]-C-lysine-
                glycine backbone (xi) SEQUENCE DESCRIPTION: SEQ ID NO: 14:

CCCCTATTGT CC                                                                12

(2) INFORMATION FOR SEQ ID NO: 15:

(i) SEQUENCE CHARACTERISTICS:
            (A) LENGTH: 12 bases
            (B) TYPE: nucleic acid
            (C) STRANDEDNESS: single
            (D) TOPOLOGY: linear (ix) FEATURE:
            (A) NAME/KEY: Modified-site
            (B) LOCATION: 1
            (D) OTHER INFORMATION:N-acetyl(2-aminoethyl)glycine backbone (ix) FEATURE:
            (A) NAME/KEY: Modified-site
            (B) LOCATION: 2
            (D) OTHER INFORMATION:N-acetyl(2-aminoethyl)glycine backbone (ix) FEATURE:
            (A) NAME/KEY: Modified-site
            (B) LOCATION: 3
            (D) OTHER INFORMATION:N-acetyl(2-aminoethyl)glycine backbone (ix) FEATURE:
            (A) NAME/KEY: Modified-site
            (B) LOCATION: 4
            (D) OTHER INFORMATION:N-acetyl(2-aminoethyl)glycine backbone (ix) FEATURE:
            (A) NAME/KEY: Modified-site
            (B) LOCATION: 5
            (D) OTHER INFORMATION:N-acetyl(2-aminoethyl)glycine backbone (ix) FEATURE:
            (A) NAME/KEY: Modified-site
            (B) LOCATION: 6
            (D) OTHER INFORMATION:N-acetyl(2-aminoethyl)glycine backbone (ix) FEATURE:
            (A) NAME/KEY: Modified-site
            (B) LOCATION: 7
            (D) OTHER INFORMATION:N-acetyl(2-aminoethyl)glycine backbone (ix) FEATURE:
            (A) NAME/KEY: Modified-site
            (B) LOCATION: 8
            (D) OTHER INFORMATION:N-acetyl(2-aminoethyl)glycine backbone (ix) FEATURE:
            (A) NAME/KEY: Modified-site
            (B) LOCATION: 9
            (D) OTHER INFORMATION:N-acetyl(2-aminoethyl)glycine backbone (ix) FEATURE:
            (A) NAME/KEY: Modified-site
            (B) LOCATION: 10
            (D) OTHER INFORMATION:N-acetyl(2-aminoethyl)glycine backbone (ix) FEATURE:
            (A) NAME/KEY: Modified-site
            (B) LOCATION: 11
            (D) OTHER INFORMATION:N-acetyl(2-aminoethyl)glycine backbone (ix) FEATURE:
            (A) NAME/KEY: Modified-site
            (B) LOCATION: 12
            (D) OTHER INFORMATION:N-[acetyl(2-aminoethyl)]-C-lysine-
                glycine backbone (xi) SEQUENCE DESCRIPTION: SEQ ID NO: 15:

```
TTCTGCCTTT CT                                                              12
```

(2) INFORMATION FOR SEQ ID NO: 16:

(i) SEQUENCE CHARACTERISTICS:
        (A) LENGTH: 8 bases
        (B) TYPE: nucleic acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION:N-acetyl(2-aminoethyl)glycine backbone (ix) FEATURE:
        (A) NAME/KEY: Modified-site
        (B) LOCATION: 2
        (D) OTHER INFORMATION:N-acetyl(2-aminoethyl)glycine backbone (ix) FEATURE:
        (A) NAME/KEY: Modified-site
        (B) LOCATION: 3
        (D) OTHER INFORMATION:N-acetyl(2-aminoethyl)glycine backbone (ix) FEATURE:
        (A) NAME/KEY: Modified-site
        (B) LOCATION: 4
        (D) OTHER INFORMATION:N-acetyl(2-aminoethyl)glycine backbone (ix) FEATURE:
        (A) NAME/KEY: Modified-site
        (B) LOCATION: 5
        (D) OTHER INFORMATION:N-acetyl(2-aminoethyl)glycine backbone (ix) FEATURE:
        (A) NAME/KEY: Modified-site
        (B) LOCATION: 6
        (D) OTHER INFORMATION:N-acetyl(2-aminoethyl)glycine backbone (ix) FEATURE:
        (A) NAME/KEY: Modified-site
        (B) LOCATION: 7
        (D) OTHER INFORMATION:N-acetyl(2-aminoethyl)glycine backbone (ix) FEATURE:
        (A) NAME/KEY: Modified-site
        (B) LOCATION: 8
        (D) OTHER INFORMATION:N-[acetyl(2-aminoethyl)]-C-lysine-
            glycine backbone (xi) SEQUENCE DESCRIPTION: SEQ ID NO: 16:

```
CTCGAGGT                                                                    8
```

(2) INFORMATION FOR SEQ ID NO: 17:

(i) SEQUENCE CHARACTERISTICS:
        (A) LENGTH: 5 bases
        (B) TYPE: nucleic acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION:N-acetyl(2-aminoethyl)glycine backbone (ix) FEATURE:
        (A) NAME/KEY: Modified-site
        (B) LOCATION: 2
        (D) OTHER INFORMATION:N-acetyl(2-aminoethyl)glycine backbone (ix) FEATURE:
        (A) NAME/KEY: Modified-site
        (B) LOCATION: 3
        (D) OTHER INFORMATION:N-acetyl(2-aminoethyl)glycine backbone

```
    (ix) FEATURE:
         (A) NAME/KEY: Modified-site
         (B) LOCATION: 4
         (D) OTHER INFORMATION:N-acetyl(2-aminoethyl)glycine backbone (ix) FEATURE:
         (A) NAME/KEY: Modified-site
         (B) LOCATION: 5
         (D) OTHER INFORMATION:N-[acetyl(2-aminoethyl)]-C-lysine-
             glycine backbone (xi) SEQUENCE DESCRIPTION: SEQ ID NO:17:

TAAAC                                                                          5

(2) INFORMATION FOR SEQ ID NO: 18:

(i) SEQUENCE CHARACTERISTICS:
        (A) LENGTH: 10 bases
        (B) TYPE: nucleic acid
        (C) STRANDEDNESS: single
        (D) TOPOLOGY: linear (ix) FEATURE:
         (A) NAME/KEY: Modified-site
         (B) LOCATION: 1
         (D) OTHER INFORMATION:N-acetyl(2-aminoethyl)glycine backbone (ix) FEATURE:
         (A) NAME/KEY: Modified-site
         (B) LOCATION: 2
         (D) OTHER INFORMATION:N-acetyl(2-aminoethyl)glycine backbone (ix) FEATURE:
         (A) NAME/KEY: Modified-site
         (B) LOCATION: 3
         (D) OTHER INFORMATION:N-acetyl(2-aminoethyl)glycine backbone (ix) FEATURE:
         (A) NAME/KEY: Modified-site
         (B) LOCATION: 4
         (D) OTHER INFORMATION:N-acetyl(2-aminoethyl)glycine backbone (ix) FEATURE:
         (A) NAME/KEY: Modified-site
         (B) LOCATION: 5
         (D) OTHER INFORMATION:N-acetyl(2-aminoethyl)glycine backbone (ix) FEATURE:
         (A) NAME/KEY: Modified-site
         (B) LOCATION: 6
         (D) OTHER INFORMATION:N-acetyl(2-aminoethyl)glycine backbone (ix) FEATURE:
         (A) NAME/KEY: Modified-site
         (B) LOCATION: 7
         (D) OTHER INFORMATION:N-acetyl(2-aminoethyl)glycine backbone (ix) FEATURE:
         (A) NAME/KEY: Modified-site
         (B) LOCATION: 8
         (D) OTHER INFORMATION:N-acetyl(2-aminoethyl)glycine backbone (ix) FEATURE:
         (A) NAME/KEY: Modified-site
         (B) LOCATION: 9
         (D) OTHER INFORMATION:N-acetyl(2-aminoethyl)glycine backbone (ix) FEATURE:
         (A) NAME/KEY: Modified-site
         (B) LOCATION: 10
         (D) OTHER INFORMATION:N-[acetyl(2-aminoethyl)]-C-lysine-
             glycine backbone (xi) SEQUENCE DESCRIPTION: SEQ ID NO:18:

AAGGAGGTGA                                                                    10
```

(2) INFORMATION FOR SEQ ID NO: 19:

(i) SEQUENCE CHARACTERISTICS:
        (A) LENGTH: 15 bases
        (B) TYPE: nucleic acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION:N-acetyl(2-aminoethyl)glycine backbone (ix) FEATURE:
        (A) NAME/KEY: Modified-site
        (B) LOCATION: 2
        (D) OTHER INFORMATION:N-acetyl(2-aminoethyl)glycine backbone (ix) FEATURE:
        (A) NAME/KEY: Modified-site
        (B) LOCATION: 3
        (D) OTHER INFORMATION:N-acetyl(2-aminoethyl)glycine backbone (ix) FEATURE:
        (A) NAME/KEY: Modified-site
        (B) LOCATION: 4
        (D) OTHER INFORMATION:N-acetyl(2-aminoethyl)glycine backbone (ix) FEATURE:
        (A) NAME/KEY: Modified-site
        (B) LOCATION: 5
        (D) OTHER INFORMATION:N-acetyl(2-aminoethyl)glycine backbone (ix) FEATURE:
        (A) NAME/KEY: Modified-site
        (B) LOCATION: 6
        (D) OTHER INFORMATION:N-acetyl(2-aminoethyl)glycine backbone (ix) FEATURE:
        (A) NAME/KEY: Modified-site
        (B) LOCATION: 7
        (D) OTHER INFORMATION:N-acetyl(2-aminoethyl)glycine backbone (ix) FEATURE:
        (A) NAME/KEY: Modified-site
        (B) LOCATION: 8
        (D) OTHER INFORMATION:(O-2-aminoethyl-O'-acetyl-
           ethylene glycol)3

(ix) FEATURE:
        (A) NAME/KEY: Modified-site
        (B) LOCATION: 9
        (D) OTHER INFORMATION:N-acetyl(2-aminoethyl)glycine backbone (ix) FEATURE:
        (A) NAME/KEY: Modified-site
        (B) LOCATION: 10
        (D) OTHER INFORMATION:N-acetyl(2-aminoethyl)glycine backbone (ix) FEATURE:
        (A) NAME/KEY: Modified-site
        (B) LOCATION: 11
        (D) OTHER INFORMATION:N-acetyl(2-aminoethyl)glycine backbone (ix) FEATURE:
        (A) NAME/KEY: Modified-site
        (B) LOCATION: 12
        (D) OTHER INFORMATION:N-acetyl(2-aminoethyl)glycine backbone (ix) FEATURE:
        (A) NAME/KEY: Modified-site
        (B) LOCATION: 13
        (D) OTHER INFORMATION:N-acetyl(2-aminoethyl)glycine backbone (ix) FEATURE:
        (A) NAME/KEY: Modified-site
        (B) LOCATION: 14

(D) OTHER INFORMATION:N-acetyl(2-aminoethyl)glycine backbone (ix) FEATURE:
    (A) NAME/KEY: Modified-site
    (B) LOCATION: 15
    (D) OTHER INFORMATION:N-[acetyl(2-aminoethyl)]-C-lysine-
        glycine backbone (xi) SEQUENCE DESCRIPTION: SEQ ID NO: 19:

TCTCTTTNTT TCTCT                                                        15

(2) INFORMATION FOR SEQ ID NO: 20:

(i) SEQUENCE CHARACTERISTICS:
     (A) LENGTH: 15 bases
     (B) TYPE: nucleic acid
     (C) STRANDEDNESS: single
     (D) TOPOLOGY: linear (ix) FEATURE:
    (A) NAME/KEY: Modified-site
    (B) LOCATION: 1
    (D) OTHER INFORMATION:N-acetyl(2-aminoethyl)glycine backbone (ix) FEATURE:
    (A) NAME/KEY: Modified-site
    (B) LOCATION: 2
    (D) OTHER INFORMATION:N-pseudo isocytosine-acetyl(2-
        aminoethyl)glycine backbone (ix) FEATURE:
    (A) NAME/KEY: Modified-site
    (B) LOCATION: 3
    (D) OTHER INFORMATION:N-acetyl(2-aminoethyl)glycine backbone (ix) FEATURE:
    (A) NAME/KEY: Modified-site
    (B) LOCATION: 4
    (D) OTHER INFORMATION:N-pseudo isocytosine-acetyl(2-
        aminoethyl)glycine backbone (ix) FEATURE:
    (A) NAME/KEY: Modified-site
    (B) LOCATION: 5
    (D) OTHER INFORMATION:N-acetyl(2-aminoethyl)glycine backbone (ix) FEATURE:
    (A) NAME/KEY: Modified-site
    (B) LOCATION: 6
    (D) OTHER INFORMATION:N-acetyl(2-aminoethyl)glycine backbone (ix) FEATURE:
    (A) NAME/KEY: Modified-site
    (B) LOCATION: 7
    (D) OTHER INFORMATION:N-acetyl(2-aminoethyl)glycine backbone (ix) FEATURE:
    (A) NAME/KEY: Modified-site
    (B) LOCATION: 8
    (D) OTHER INFORMATION:(O-2-aminoethyl-O'-acetyl-
        ethylene glycol)3

(ix) FEATURE:
    (A) NAME/KEY: Modified-site
    (B) LOCATION: 9
    (D) OTHER INFORMATION:N-acetyl(2-aminoethyl)glycine backbone (ix) FEATURE:
    (A) NAME/KEY: Modified-site
    (B) LOCATION: 10
    (D) OTHER INFORMATION:N-acetyl(2-aminoethyl)glycine backbone (ix) FEATURE:
    (A) NAME/KEY: Modified-site
    (B) LOCATION: 11
    (D) OTHER INFORMATION:N-acetyl(2-aminoethyl)glycine backbone

```
        (ix) FEATURE:
              (A) NAME/KEY: Modified-site
              (B) LOCATION: 12
              (D) OTHER INFORMATION:N-acetyl(2-aminoethyl)glycine backbone (ix) FEATURE:
              (A) NAME/KEY: Modified-site
              (B) LOCATION: 13
              (D) OTHER INFORMATION:N-acetyl(2-aminoethyl)glycine backbone (ix) FEATURE:
              (A) NAME/KEY: Modified-site
              (B) LOCATION: 14
              (D) OTHER INFORMATION:N-acetyl(2-aminoethyl)glycine backbone (ix) FEATURE:
              (A) NAME/KEY: Modified-site
              (B) LOCATION: 15
              (D) OTHER INFORMATION:N-[acetyl(2-aminoethyl)]-C-lysine-
                  glycine backbone (xi) SEQUENCE DESCRIPTION: SEQ ID NO: 20:

TNTNTTTNTT TCTCT                                                            15

(2) INFORMATION FOR SEQ ID NO: 21:

(i) SEQUENCE CHARACTERISTICS:
              (A) LENGTH: 27 bases
              (B) TYPE: nucleic acid
              (C) STRANDEDNESS: single
              (D) TOPOLOGY: linear (xi) SEQUENCE DESCRIPTION: SEQ ID NO:21:

AAAGGAAGAG UAUGAGUAUU CAACAUU                                               27

(2) INFORMATION FOR SEQ ID NO: 22:

(i) SEQUENCE CHARACTERISTICS:
              (A) LENGTH: 27 bases
              (B) TYPE: nucleic acid
              (C) STRANDEDNESS: single
              (D) TOPOLOGY: linear (xi) SEQUENCE DESCRIPTION: SEQ ID NO:22:

AAAGGAAGAC AAUGAGUAUU CAACAUU                                               27

(2) INFORMATION FOR SEQ ID NO: 23:

(i) SEQUENCE CHARACTERISTICS:
              (A) LENGTH: 27 bases
              (B) TYPE: nucleic acid
              (C) STRANDEDNESS: single
              (D) TOPOLOGY: linear (xi) SEQUENCE DESCRIPTION: SEQ ID NO:23:

AAAGGAGGCC UAUGUCGAUU CAACAUU                                               27
```